US006406888B1

(12) United States Patent
Conklin et al.

(10) Patent No.: US 6,406,888 B1
(45) Date of Patent: Jun. 18, 2002

(54) HELICAL CYTOKINE ZALPHA33

(75) Inventors: Darrell C. Conklin, Seattle; Zeren Gao, Redmond, both of WA (US)

(73) Assignee: ZymoGenetics, Inc., Seattle, WA (US)

( * ) Notice: Subject to any disclaimer, the term of this patent is extended or adjusted under 35 U.S.C. 154(b) by 33 days.

(21) Appl. No.: 09/593,995

(22) Filed: Jun. 14, 2000

Related U.S. Application Data

(60) Provisional application No. 60/139,121, filed on Jun. 14, 1999.

(51) Int. Cl.⁷ .......................... C12N 15/00; C12N 15/63

(52) U.S. Cl. ................ 435/69.5; 435/320.1; 435/252.3; 435/325; 435/6; 530/351; 530/536; 530/23.5

(58) Field of Search ............................. 435/69.5, 320.1, 435/325, 252.3, 6; 536/23.1, 23.5; 530/351

(56) References Cited

PUBLICATIONS

Marra et al. Locus AA122535, Feb. 17, 1997. Accessed Jan. 19, 2002 (see attached computer printout).*
Hillier et al., EST 250621, Acc. No. R73763, Jun. 5, 1995.
Hillier et al., EST 250534, Acc. No. R73676, Jun. 5, 1995.
Hillier et al., EST 264823, Acc. No. H04943, Jun. 21, 1995.
LIFESEQ™ Clone Information Results (INC043226), Incyte Pharmaceuticals, Inc., Aug. 25, 1995.
LIFESEQ™ Clone Information Results (INC008869), Incyte Pharmaceuticals, Inc., Aug. 25, 1995.
LIFESEQ™ Clone Information Results (INC004893), Incyte Pharmaceuticals, Inc., Aug. 25, 1995.
LIFESEQ™ Clone Information Results (INC411704), Incyte Pharmaceuticals, Inc., Aug. 25, 1995.
LIFESEQ™ Clone Information Results (INC377919), Incyte Pharmaceuticals, Inc., Aug. 25, 1995.
LIFESEQ™ Clone Information Results (INC373913), Incyte Pharmaceuticals, Inc., Aug. 25, 1995.
LIFESEQ™ Clone Information Results (INC385566), Incyte Pharmaceuticals, Inc., Oct. 6, 1995.
LIFESEQ™ Clone Information Results (INC542785), Incyte Pharmaceuticals, Inc., Nov. 8, 1995.
LIFESEQ™ Clone Information Results (INC608629), Incyte Pharmaceuticals, Inc., Dec. 4, 1995.
LIFESEQ™ Clone Information Results (INC1231350), Incyte Pharmaceuticals, Inc., May 20, 1996.
LIFESEQ™ Clone Information Results (INC1375929), Incyte Pharmaceuticals, Inc., Jun. 18, 1996.
LIFESEQ™ Clone Information Results (INC1830410), Incyte Pharmaceuticals, Inc., Sep. 11, 1996.
Hillier et al., EST 753117, Acc. No. AA115024, Nov. 15, 1996.
Hillier et al., EST 753007, Acc. No. AA115496, Nov. 15, 1996.
LIFESEQ™ Clone Information Results (INC2110942), Incyte Pharmaceuticals, Inc., Dec. 9, 1996.

LIFESEQ™ Clone Information Results (INC2725558), Incyte Pharmaceuticals, Inc., Feb. 4, 1997.
Liew, EST 855579, Acc. No. AA216282, Feb. 4, 1997.
LIFESEQ™ Clone Information Results (LIN608629T6), Incyte Pharmaceuticals, Inc., Feb. 28, 1997.
LIFESEQ™ Clone Information Results (LIN1830410F6), Incyte Pharmaceuticals, Inc., Feb. 28, 1997.
LIFESEQ™ Clone Information Results (LIN1830410T6), Incyte Pharmaceuticals, Inc., Feb. 28, 1997.
LIFESEQ™ Clone Information Results (INC2722733), Incyte Pharmaceuticals, Inc., Mar. 10, 1997.
Hillier et al., EST 924714, Acc. No. AA284743, Apr. 2, 1997.
Hillier et al., EST 924715, Acc. No. AA284744, Apr. 2, 1997.
Adams et al, EST 1024787, Acc. No. AA383418, Apr. 21, 1997.
Hillier et al., EST 1103609, Acc. No. AA459087, Jun. 9, 1997.
Hillier et al., EST 1103415, Acc. No. AA458893, Jun. 9, 1997.
TIGR Tentative Human Consensus Sequence, THC AA074269, Jul. 3, 1997.
TIGR Tentative Human Consensus Sequence, THC TH213868, Jul. 3, 1997.
TIGR Tentative Human Consensus Sequence, THC THC198964, Jul. 3, 1997.
LIFESEQ™ Clone Information Results (INC3422375), Incyte Pharmaceuticals, Inc., Jul. 8, 1997.
LIFESEQ™ Clone Information Results (INC2971676), Incyte Pharmaceuticals, Inc., Jul. 8, 1997.
Strausberg, EST 1166136, Acc. No. AA521496, Jul. 16, 1997.
Hillier et al., EST 709463, Acc. No. AA074269, Oct. 27, 1997.
LIFESEQ™ Clone Information Results (INC3674406), Incyte Pharmaceuticals, Inc., Nov. 17, 1997.
Strausberg, EST 1452377, Acc. No. AA736928, Jan. 6, 1998.
LIFESEQ™ Clone Information Results (INC3679206), Incyte Pharmaceuticals, Inc., Jan. 9, 1998.
Strausberg, EST 1428676, Acc. No. AA721340, Jan. 16, 1998.
Strausberg, EST 1461429, Acc. No. AA743717, Jan. 16, 1998.

(List continued on next page.)

Primary Examiner—Lorraine Spector
Assistant Examiner—Dong Jiang
(74) Attorney, Agent, or Firm—Gary E. Parker

(57) ABSTRACT

Novel cytokine polypeptides, materials and methods for making them, and method of use are disclosed. The polypeptides comprise at least nine contiguous amino acid residues of SEQ ID NO:2 or SEQ ID NO:4, and may be prepared as polypeptide fusions comprise heterologous sequences, such as affinity tags. The polypeptides and polynucleotides encoding them may be used within a variety of therapeutic, diagnostic, and research applications.

10 Claims, 5 Drawing Sheets

PUBLICATIONS

Strausberg, EST 1478889, Acc. No. AA757146, Jan. 23, 1998.
Strausberg, EST 1534066, Acc. No. AA812233, Feb. 12, 1998.
Strausberg, EST 1533216, Acc. No. AA811383, Feb. 12, 1998.
Strausberg, EST 1573463, Acc. No. AA847935, Mar. 25, 1998.
Strausberg, EST 1632382, Acc. No. AA904351, Apr. 13, 1998.
Hillier et al., EST 1727241, Acc. No. AA989606, Jun. 2, 1998.
Strausberg, EST 176836, Acc. No. AI0126938, Jun. 18, 1998.
LIFESEQ™ Clone Information Results (INC4569666), Incyte Pharmaceuticals, Inc., Aug. 17, 1998.
Strausberg, EST 1908455, Acc. No. AI149753, Sep. 30, 1998.
Strausberg, EST 1947915, Acc. No. AI184166, Oct. 9, 1998.
Strausberg, EST 2126194, Acc. No. AI342452, Dec. 29, 1998.
Strausberg, EST 2227059, Acc. No. AI419303, Feb. 10, 1999.
LIFESEQ™ Clone Information Results (INC4544570), Incyte Pharmaceuticals, Inc., Mar. 15, 1999.
LIFESEQ™ Clone Information Results (INC4545426), Incyte Pharmaceuticals, Inc., Mar. 15, 1999.
LIFESEQ™ Clone Information Results (INC4598372), Incyte Pharmaceuticals, Inc., Mar. 15, 1999.
Marra et al., EST 561081, Acc. No. W54026, Jun. 3, 1996.
Marra et al., EST 637279, Acc. No. AA023381, Aug. 9, 1996.
Marra et al., EST 678109, Acc. No. AA052479, Sep. 13, 1996.
Marra et al., EST 761727, Acc. No. AA122535, Nov. 21, 1996.
Marra et al., EST 836736, Acc. No. AA197608, Jan. 22, 1997.
Marra et al., EST 917712, Acc. No. AA275701, Apr. 1, 1997.
Marra et al., EST 1066959, Acc. No. AA422589, May 8, 1997.
Marra et al., EST 1192547, Acc. No. AA546498, Aug. 5, 1997.
Marra et al., EST 1312648, Acc. No. AA616024, Oct. 7, 1997.
Marra et al., EST 1377975, Acc. No. AA672389, Nov. 25, 1997.
Marra et al., EST 1377927, Acc. No. AA672341, Nov. 25, 1997.
Marra et al., EST 1387745, Acc. No. AA681545, Dec. 5, 1997.
Marra et al., EST 1561721, Acc. No. AA839589, Feb. 27, 1998.
Marra et al., EST 1623624, Acc. No. AA895593, Apr. 6, 1998.
Marra et al., EST 1672543, Acc. No. AA940086, May 1, 1998.
Ko et al., EST 1835273, Acc. No. AU023213, Aug. 11, 1998.
Marra et al., EST 1958635, Acc. No. AI194888, Oct. 14, 1998.
Marra et al., EST 1958613, Acc. No. AI194866, Oct. 14, 1998.
Marra et al., EST 2028233, Acc. No. AI255149, Nov. 12, 1998.
Marra et al., EST 2081005, Acc. No. AI303942, Dec. 7, 1998.
Marra et al., EST 2081065, Acc. No. AI304002, Dec. 7, 1998.
Marra et al., EST 2262119, Acc. No. AI452272, Feb. 24, 1999.
Marra et al., EST 2425279, Acc. No. AI606731, Apr. 15, 1999.

* cited by examiner

Human:  MSTPPLAASGMAPGPFAGPQAQQAAREVNTASLCRIGQETVQDIVY
Mouse:  MSTPPLAPTGMASGPFGGPQAQQAAREVNTATLCRIGQETVQDIVY RTMEIFQLLRNMQLPNGVTYHTGTYQDRLTKLQDNLRQLSVLFRKLRLVYDKCN
RTMEIFQLLRNMQLPNGVTYHTGTYQDRLTKLQDHLRQLSILFRKLRLVYDKCN ENCGGMDPIPVEQLIPYVEEDGSKNDDRAGPPRFASEERREIAEVNKKLKQKNQ
ENCGGMDPIPVEQLIPYVDEDGSKNDDRAGPPRFASEERREIVEVNKKLKQKNQ

QLKQIMDQLRNLIWDINAMLAMRN
QLKQIMDQLRNLIWDINAMLAMRN

Fig. 2

SEQUENCE LISTING

```
<160> NUMBER OF SEQ ID NOS: 10

<210> SEQ ID NO 1
<211> LENGTH: 954
<212> TYPE: DNA
<213> ORGANISM: Homo sapiens
<220> FEATURE:
<221> NAME/KEY: CDS
<222> LOCATION: (136)...(672)

<400> SEQUENCE: 1
gccgctgttt tgaaatcggg ccgcgggggg tctctcaagc tggttccaac g ctgaggccc    60 cacagcctcc caattccggg cagaccctg acacctgctg tctggcccct t ccggcctga   120
```

```
agctgcagcc gcgcc atg tcc acc cct ccg ttg gcc gcg tcg ggg atg gcg         171
               Met Ser Thr Pro Pro Leu Ala Ala Ser Gly Met Ala
                 1               5                  10 ccc ggg ccc ttc gcc ggg ccc cag gct cag c ag gcc gcc cgg gaa gtc         219
Pro Gly Pro Phe Ala Gly Pro Gln Ala Gln G ln Ala Ala Arg Glu Val
         15                  20                  25 aac acg gcg tcg ctg tgc cgc atc ggg cag g ag aca gtg cag gac atc         267
Asn Thr Ala Ser Leu Cys Arg Ile Gly Gln G lu Thr Val Gln Asp Ile
 30                  35                  40 gtg tac cgc acc atg gag atc ttc cag ctc c tg agg aac atg cag ctg         315
Val Tyr Arg Thr Met Glu Ile Phe Gln Leu L eu Arg Asn Met Gln Leu
 45                  50                  55                  60 cca aat ggt gtc act tac cac act gga aca t at caa gac cgg tta aca         363
Pro Asn Gly Val Thr Tyr His Thr Gly Thr T yr Gln Asp Arg Leu Thr
                 65                  70                  75 aag cta cag gat aat ctt cgc caa ctt tca g tt ctc ttc agg aag ctg         411
Lys Leu Gln Asp Asn Leu Arg Gln Leu Ser V al Leu Phe Arg Lys Leu
                     80                  85                  90 aga ttg gta tat gac aaa tgc aat gaa aac t gt ggt ggg atg gat ccc         459
Arg Leu Val Tyr Asp Lys Cys Asn Glu Asn C ys Gly Gly Met Asp Pro
             95                  100                 105 att cca gtc gag caa ctt att cca tat gtg g aa gaa gat ggc tca aag        507
Ile Pro Val Glu Gln Leu Ile Pro Tyr Val G lu Glu Asp Gly Ser Lys
        110                 115                 120 aat gat gat cgg gct ggc cca cct cgt ttt g ct agt gaa gag agg cga        555
Asn Asp Asp Arg Ala Gly Pro Pro Arg Phe A la Ser Glu Glu Arg Arg
125                 130                 135                 140 gaa att gct gaa gta aat aaa aaa ctc aaa c ag aag aat caa cag ctg        603
Glu Ile Ala Glu Val Asn Lys Lys Leu Lys G ln Lys Asn Gln Gln Leu
                145                 150                 155 aaa caa att atg gat caa tta cga aat ctc a tc tgg gat ata aat gcc        651
Lys Gln Ile Met Asp Gln Leu Arg Asn Leu I le Trp Asp Ile Asn Ala
            160                 165                 170 atg ttg gca atg agg aac taa gctgatattt aaatttcc tg ctttacacat          702
Met Leu Ala Met Arg Asn  *
                175 gttataccat tgtttttttcc ctcaagtatt ttttccctgt gaagaagatt a tttatctgc    762 ttttatttta gtcactaaaa ctaaagtttt tattttttaca ttgtgatttt t acattaaaa    822 tattaacttt tttaatgcta ttttatgaaa gattattgta ataaactttg a tggggtttg    882 tattttggtt aatcttcatg aattgaataa ttgtttttttt aaagcaaaat a aagttttttt  942 aaataaatgt ta                                                           954

<210> SEQ ID NO 2
<211> LENGTH: 178
<212> TYPE: PRT
<213> ORGANISM: Homo sapiens

<400> SEQUENCE: 2

Met Ser Thr Pro Pro Leu Ala Ala Ser Gly M et Ala Pro Gly Pro Phe
 1               5                  10                  15

Ala Gly Pro Gln Ala Gln Gln Ala Ala Arg G lu Val Asn Thr Ala Ser
                20                  25                  30

Leu Cys Arg Ile Gly Gln Glu Thr Val Gln A sp Ile Val Tyr Arg Thr
            35                  40                  45

Met Glu Ile Phe Gln Leu Leu Arg Asn Met G ln Leu Pro Asn Gly Val
        50                  55                  60

Thr Tyr His Thr Gly Thr Tyr Gln Asp Arg L eu Thr Lys Leu Gln Asp
```

```
                65                 70                 75                 80
Asn Leu Arg Gln Leu Ser Val Leu Phe Arg Lys Leu Arg Leu Val Tyr
                    85                 90                 95
Asp Lys Cys Asn Glu Asn Cys Gly Gly Met Asp Pro Ile Pro Val Glu
                100                105                110
Gln Leu Ile Pro Tyr Val Glu Glu Asp Gly Ser Lys Asn Asp Asp Arg
            115                120                125
Ala Gly Pro Pro Arg Phe Ala Ser Glu Glu Arg Arg Glu Ile Ala Glu
        130                135                140
Val Asn Lys Lys Leu Lys Gln Lys Asn Gln Gln Leu Lys Gln Ile Met
145                150                155                160
Asp Gln Leu Arg Asn Leu Ile Trp Asp Ile Asn Ala Met Leu Ala Met
                165                170                175
Arg Asn

<210> SEQ ID NO 3
<211> LENGTH: 950
<212> TYPE: DNA
<213> ORGANISM: Mus musculus
<220> FEATURE:
<221> NAME/KEY: CDS
<222> LOCATION: (120)...(656)

<400> SEQUENCE: 3
cactgttggc ctactggagt cttccggtac agcgcttgca tcgcggcggg c ggaagtggc      60 gccgcttttt tgaaatcggc cgagtgggct cgcgccggac ccgagccgcc g ggggtgcc     119 atg tcc acc cct ccg ctg gcg ccc acg ggc a tg gcg tcc ggg ccc ttc     167
Met Ser Thr Pro Pro Leu Ala Pro Thr Gly Met Ala Ser Gly Pro Phe
 1               5                  10                  15 ggc ggc ccg cag gct cag cag gcc gcg cgc g ag gtc aac acg gcc acg     215
Gly Gly Pro Gln Ala Gln Gln Ala Ala Arg Glu Val Asn Thr Ala Thr
                20                  25                  30 ctg tgc cgc atc ggg cag gag acc gtg cag g ac atc gtg tac cgc acc     263
Leu Cys Arg Ile Gly Gln Glu Thr Val Gln Asp Ile Val Tyr Arg Thr
            35                  40                  45 atg gag atc ttc cag ctg ctc agg aac atg c ag ctg cca aat ggt gtc     311
Met Glu Ile Phe Gln Leu Leu Arg Asn Met Gln Leu Pro Asn Gly Val
        50                  55                  60 act tac cat act gga act tac caa gac cgg c ta aca aag ctg cag gac     359
Thr Tyr His Thr Gly Thr Tyr Gln Asp Arg Leu Thr Lys Leu Gln Asp
 65                 70                  75                  80 cac ctt cgg caa ctt tct att ctc ttc agg a ag ctg cga ctg gtc tat     407
His Leu Arg Gln Leu Ser Ile Leu Phe Arg Lys Leu Arg Leu Val Tyr
                    85                  90                  95 gac aaa tgt aat gag aac tgt ggt ggg atg g ac ccc att cct gtt gag     455
Asp Lys Cys Asn Glu Asn Cys Gly Gly Met Asp Pro Ile Pro Val Glu
                100                 105                 110 caa ctg att cca tat gtg gat gaa gat ggc t ca aag aac gac gac cgg     503
Gln Leu Ile Pro Tyr Val Asp Glu Asp Gly Ser Lys Asn Asp Asp Arg
            115                 120                 125 gct ggt cca cct cgt ttt gct agc gaa gag a ga cga gaa att gta gaa     551
Ala Gly Pro Pro Arg Phe Ala Ser Glu Glu Arg Arg Glu Ile Val Glu
        130                 135                 140 gta aat aag aaa ctc aaa cag aag aat caa c ag ctg aag cag att atg     599
Val Asn Lys Lys Leu Lys Gln Lys Asn Gln Gln Leu Lys Gln Ile Met
145                 150                 155                 160 gat caa tta cgg aat ctc atc tgg gac ata a at gcc atg ctg gca atg     647
Asp Gln Leu Arg Asn Leu Ile Trp Asp Ile Asn Ala Met Leu Ala Met
```

-continued

```
                       165                 170                 175
agg aac taa agcgatattt aaatctcctg ctctactcat gtgatgaa gt           696
Arg Asn * tgggtttttc ccccctcttg agtattcctc cctttgaaaa acgttattta t gtctttatt  756 ttaacagcta gcactaaagt ttctgttttc actttaaagt atttactagc t tttttttta  816 atactgtggg ttttatgaaa gattattgta ataccttga tagggtataa a ttttggtta   876 atcttcagaa attgaataaa ttaaaaaata caaataaaaa tttaaaaaaa a aaaaaaaaa  936 aaaggccaca tgtg                                                    950
```

<210> SEQ ID NO 4
<211> LENGTH: 178
<212> TYPE: PRT
<213> ORGANISM: Mus musculus

<400> SEQUENCE: 4

```
Met Ser Thr Pro Pro Leu Ala Pro Thr Gly M et Ala Ser Gly Pro Phe
 1               5                  10                  15

Gly Gly Pro Gln Ala Gln Gln Ala Ala Arg G lu Val Asn Thr Ala Thr
            20                  25                  30

Leu Cys Arg Ile Gly Gln Glu Thr Val Gln A sp Ile Val Tyr Arg Thr
        35                  40                  45

Met Glu Ile Phe Gln Leu Leu Arg Asn Met G ln Leu Pro Asn Gly Val
    50                  55                  60

Thr Tyr His Thr Gly Thr Tyr Gln Asp Arg L eu Thr Lys Leu Gln Asp
65                  70                  75                  80

His Leu Arg Gln Leu Ser Ile Leu Phe Arg L ys Leu Arg Leu Val Tyr
                85                  90                  95

Asp Lys Cys Asn Glu Asn Cys Gly Gly Met A sp Pro Ile Pro Val Glu
            100                 105                 110

Gln Leu Ile Pro Tyr Val Asp Glu Asp Gly S er Lys Asn Asp Asp Arg
        115                 120                 125

Ala Gly Pro Pro Arg Phe Ala Ser Glu Glu A rg Arg Glu Ile Val Glu
    130                 135                 140

Val Asn Lys Lys Leu Lys Gln Lys Asn Gln G ln Leu Lys Gln Ile Met
145                 150                 155                 160

Asp Gln Leu Arg Asn Leu Ile Trp Asp Ile A sn Ala Met Leu Ala Met
                165                 170                 175

Arg Asn
```

<210> SEQ ID NO 5
<211> LENGTH: 178
<212> TYPE: PRT
<213> ORGANISM: Artificial Sequence
<220> FEATURE:
<223> OTHER INFORMATION: variant polypeptides
<221> NAME/KEY: VARIANT
<222> LOCATION: (41)...(45)
<223> OTHER INFORMATION: Xaa is Leu, Ile, Va l, Met, Phe, Trp, Gly, or
      Ala
<221> NAME/KEY: VARIANT
<222> LOCATION: (48)...(48)
<223> OTHER INFORMATION: Xaa is Thr, Leu, Il e, Val, Met, Phe, Trp, Gly,
      or Ala
<221> NAME/KEY: VARIANT
<222> LOCATION: (51)...(78)
<223> OTHER INFORMATION: Xaa is Leu, Ile, Va l, Met, Phe, Trp, Gly, or
      Ala
<221> NAME/KEY: VARIANT
<222> LOCATION: (81)...(81)

```
<223> OTHER INFORMATION: Xaa is Asn, Leu, Ile, Val, Met, Phe, Trp, Gly,
      Ala, or His
<221> NAME/KEY: VARIANT
<222> LOCATION: (82)...(118)
<223> OTHER INFORMATION: Xaa is Leu, Ile, Val, Met, Phe, Trp, Gly, or
                         Ala
<221> NAME/KEY: VARIANT
<222> LOCATION: (121)...(121)
<223> OTHER INFORMATION: Xaa is Asp, Leu, Ile, Val, Met, Phe, Trp, Gly,
                         or Ala
<221> NAME/KEY: VARIANT
<222> LOCATION: (122)...(122)
<223> OTHER INFORMATION: Xaa is Leu, Ile, Val, Met, Phe, Trp, Gly, or
                         Ala
<221> NAME/KEY: VARIANT
<222> LOCATION: (125)...(125)
<223> OTHER INFORMATION: Xaa is Asn, Leu, Ile, Val, Met, Phe, Trp, Gly,
                         or Ala
<221> NAME/KEY: VARIANT
<222> LOCATION: (149)...(149)
<223> OTHER INFORMATION: Xaa is Leu, Ile, Val, Met, Phe, Trp, Gly, or
                         Ala
<221> NAME/KEY: VARIANT
<222> LOCATION: (152)...(152)
<223> OTHER INFORMATION: Xaa is Lys, Leu, Ile, Val, Met, Phe, Trp, Gly,
                         or Ala
<221> NAME/KEY: VARIANT
<222> LOCATION: (153)...(153)
<223> OTHER INFORMATION: Xaa is Asn, Leu, Ile, Val, Met, Phe, Trp, Gly,
                         or Ala
<221> NAME/KEY: VARIANT
<222> LOCATION: (156)...(163)
<223> OTHER INFORMATION: Xaa is Leu, Ile, Val, Met, Phe, Trp, Gly, or
                         Ala

<400> SEQUENCE: 5

Met Ser Thr Pro Pro Leu Ala Ala Ser Gly Met Ala Pro Gly Pro Phe
 1               5                  10                  15

Ala Gly Pro Gln Ala Gln Gln Ala Ala Arg Glu Val Asn Thr Ala Ser
            20                  25                  30

Leu Cys Arg Ile Gly Gln Glu Thr Xaa Gln Asp Xaa Xaa Tyr Arg Xaa
        35                  40                  45

Met Glu Xaa Xaa Gln Leu Xaa Arg Asn Met Gln Leu Pro Asn Gly Val
    50                  55                  60

Thr Tyr His Thr Gly Thr Tyr Gln Asp Arg Leu Thr Lys Xaa Gln Asp
65                  70                  75                  80

Xaa Xaa Arg Gln Xaa Ser Val Xaa Xaa Arg Lys Xaa Arg Leu Val Tyr
                85                  90                  95

Asp Lys Cys Asn Glu Asn Cys Gly Gly Met Asp Pro Ile Pro Xaa Glu
            100                 105                 110

Gln Xaa Xaa Pro Tyr Xaa Glu Glu Xaa Xaa Ser Lys Xaa Asp Asp Arg
        115                 120                 125

Ala Gly Pro Pro Arg Phe Ala Ser Glu Glu Arg Arg Glu Ile Ala Glu
    130                 135                 140

Val Asn Lys Lys Xaa Lys Gln Xaa Xaa Gln Gln Xaa Lys Gln Xaa Xaa
145                 150                 155                 160

Asp Gln Xaa Arg Asn Leu Ile Trp Asp Ile Asn Ala Met Leu Ala Met
                165                 170                 175

Arg Asn

<210> SEQ ID NO 6
<211> LENGTH: 534
<212> TYPE: DNA
<213> ORGANISM: Artificial Sequence
<220> FEATURE:
<223> OTHER INFORMATION: degenerate sequence
```

<221> NAME/KEY: misc_feature
<222> LOCATION: (1)...(534)
<223> OTHER INFORMATION: n = A,T,C or G

<400> SEQUENCE: 6

| | | | | | |
|---|---|---|---|---|---|
| atgwsnacnc | cnccnytngc | ngcnwsnggn | atggcnccng | gnccnttygc n | ggnccncar -continued

| | | | | |
|---|---|---|---|---|
| ttgtcgggcg | tggtggcggg | cgcctgtagt | cccagctact cggaggccg a | ggctggaga | 360 |
| atggtgtgaa | cccgggaggc | ggagcttgca | gtgagccgag gtcgcgccac t | gcactccag | 420 |
| cctgggtgac | agagcgagac | tccatctcaa | aagaaaaag aaaaaaaat c | agacactaa | 480 |
| taagagccag | agtcagaaag | aagtgtgtgt | gttgatcatt tttttgctt a | cagatactg | 540 |
| ggaaaactca | agaataaaa | catctgagca | gggaccaaga gcaatcgggg a | gtccgtatc | 600 |
| atgtcacaga | gaagcgtaca | agcttaggaa | tcttgttttc tgaattcgaa t | cgcaggttg | 660 |
| ccagttacac | ctgtatgcga | ctcaacaagt | actttaacct gtctcttagc t | gttatacta | 720 |
| caaacctcag | gcttgttaag | agaaaatgct | ccgcaaggaa ctaaacacag a | aggttctaa | 780 |
| cgctgagcca | agactgggaa | acgaactctg | gaactcacc ccaggctccc c | aagaacatc | 840 |
| gcccctctgg | ctggagcgca | attggtgatt | ggctacttaa cccgtccgtc c | tttcccgcc | 900 |
| cagggggtcca | atccaatcca | gcccggctcc | gctcggagac agttcgccga g | tgggcggtg | 960 |
| tctatgacgt | tttctgacgt | gttacgtcac | agtgggcgga agtcgcggcc g | ctgttttga | 1020 |
| aatcgggccg | cgggggggtct | ctcaagctgg | ttccaacgct gaggcccac a | gcctcccaa | 1080 |
| ttccgggcag | accctgaca | cctgctgtct | ggccccttcc ggcctgaagc t | gcagccgcg | 1140 |
| ccatgtccac | ccctccgttg | gccgcgtcgg | ggatggcgcc cgggccttc g | ccgggcccc | 1200 |
| aggctcagca | ggccgcccgg | gaagtcaaca | cggcgtcgct gtgccgcatc g | ggcaggaga | 1260 |
| cagtgcagga | catcgtgtac | cgcaccatgg | agatcttcca gctcctgagg a | acatgcagg | 1320 |
| taggaaggcg | ggcgcgcgag | gccaggggga | tgcagctggg agggaaaggg c | ctctggttt | 1380 |
| cctctttacg | tgggggcccgt | ggatgtcatc | ggggctgccc tggcaaacc t | taggtgtag | 1440 |
| ggtctccccc | attcacactc | aagagtgtcc | ccaaaagtcg gatttgtaga g | gtgatgttt | 1500 |
| tccagaccag | atttctgcag | aattgaagcc | aatttttttt agattcaatc g | agctctta | 1560 |
| gttactctgt | aaactcttgc | accttcaag | gcagagatgg gtcgcactcc a | cttccctct | 1620 |
| ttaggttgct | ttaaatgttt | tttccagcat | ttcttctggg gaggtccaag g | agttgaaga | 1680 |
| atttacattt | tttttaaaaa | aacagtcctc | cttttttttgg catagttaat a | tacagtaaa | 1740 |
| ctacactcac | ctaaagtttt | gatatatatg | tgtactgtag tctgtatact t | gtgaaatta | 1800 |
| tcaccacaat | caaaatagtg | tacacatcat | cccagaaagt ttcttcatac c | cctctgaca | 1860 |
| tctttgcttc | ccaccttcca | tcgctaagca | accattgatc tgcgttctgt a | atcataaat | 1920 |
| taatttgcat | ttgctagggt | tttatataaa | cggagtctac agtatgtggg c | tttttttt | 1980 |
| tgtctgagat | ccttcactaa | gaatgcatca | ataatttcct ttttattgct g | agtaatgtt | 2040 |
| ccattgtatc | catgtatcac | catttgccta | ccttttcttc tgttgatgga c | atttgggtt | 2100 |
| gtttccactt | tttggctgtt | gtaaataatg | ctgctatgaa cttttgctga c | aaattttg | 2160 |
| tgtgaacgta | tgtgtcattt | ctcttggaca | gattcaggag tggaattgct g | gatcatgca | 2220 |
| gtacatgtct | gtttaatact | ttaagaaact | tttccaaagt ggcctgagcc a | ttttacgtc | 2280 |
| ccgattattg | ctagtgggaa | tgtaaacatt | gctgtttgag ggttctagtt t | ctcctcatc | 2340 |
| ctcatcaaca | cctgttatgt | cttgatgctt | tccaaatact tctcccagtc t | atcctgcct | 2400 |
| ttttattctc | ttaatactgt | cttttgaaga | acagacattt taaatttga t | ggaatccag | 2460 |
| cttactgatt | tgttctttta | tagattttgg | ttttgctgtc atacctaaga a | atctttgcc | 2520 |
| taacccaagg | tgacaaaggg | tttctgtttt | cttctagaag ttttgtactt t | caagcttta | 2580 |
| tatttaggtc | tacaacctat | atttagtttt | gtgagttttt aaatatgtat a | catagtggc | 2640 |
| agatacggat | ccaagttcat | tgttttgcat | ttggatatcc agttgttcca g | caccatttt | 2700 |

-continued

```
gctgacccat ttttaatgct tgcttatatt acccactaca tgtagtagat a ttatttttg   2760 ttttacagat gaagattctg tacttcagag agataaagtg acttgcccaa a cctagtcag   2820 tggtagggta aatttgaaac caagttttca aaaatcttac agctcttatt t ctgtgggtg   2880 tccaaaaaag tgttttattg cttttttttt ttttaactgg tcaagacttt t ttttcgtc    2940 ctgattataa gagtaattca gtttcgtgga aattttttaag accatgtgaa a tatagtaca  3000 aaggagatcc aggagaaatt atgacattct ttggcaataa tttaaaaaaa t gaatagatt   3060 catatctaga atgaataaag tacggattaa ataatgtctc agaatttagc a tactttaaa   3120 aaaaattttg tcctgttata tgcaaagcac cgaataatac ctaacactta c gaagtactt   3180 tccttggtca ggtaccctgt tataggagca gttttaagga gtattttat c cctatttta   3240 cagtaaagga aactgaggct taatgagaga aaaataaat tacccaacat c acacacgac   3300 taatagctct tcctactaac ctcttttttaa tactaacttg ctgtcaatgt a cattattaa   3360 aagatataat acaggttcat gttctacgca gaactaaact ttttcaaaaa a gtattttta   3420 tcaataacta gattacatgt ggacctgcat tcaaagccaa ctttttttttt t ttaagtttt   3480 ttttttttgt ctgtaagttt attcaatgca aaataatcct ctccaattttt a ctgaggtgg   3540 ctgaccatgt ccacgaccaa atccgcctct aaactggaat tcggttgttg a cccagcccc   3600 agtctcggct ttcttgtcgg caccagggggg cacagcactc cgtctgtagg t atctctgtc  3660 ggcttcccct cttgtgagtc ttgcaggtcg ctcaccctcc agacctttag g ctgaggcct   3720 gccagtctct ggacggctgc ggcgtagggt ggcaggaaca atctccgggg g cagatgaag   3780 gtaatcacag agatactgga taccctcatt ggtaaggtac cagtagaaat g tctccaggc   3840 aaactgttcc ttcacgtagc ctcaggactt gagaaactgc atggccttca t gacatgaag   3900 gttggacaca ttcttgtctg ccagctccgg gtgcttaggc atgtggaatc c tccttggcc   3960 accatgattc cctccttaaa aaggagttca taggctaggc gcggtggctc a cgcctgtaa   4020 tcccagcact ttgagaggcc gaggtgggcg atcacgagg tcaggaattc g agaccagcc    4080 tagccaacat ggtgaaaccc catctctact aaaaatacaa aaattagccg g gcgtggtgg   4140 cgggcgcctg taatcccagc tactcgggag gctggggcag gagaatcgct t gaacccggg   4200 aggcggaggt ggcagtgagc cgagagatcg cgccactgca ctccaggctg g cgacagag    4260 cgagactctg tctcaagaaa aaggagttca taaatggcaa tacgtttctt c ttaagcttc   4320 aacatttcgg ccactgtagg tctgggaccc aaagccagct tttgagggac t atgataatt   4380 atatgtgtgc ttttcatttt gtgaaatctg tgatcactca tccaggacct t tggggccta   4440 tcataattgg ctgaaaagat aacaatgggc tccttcattt ccaaaaaaac t agaagaggt   4500 gatagaaata ggatattctt aactatatat aacctagtga tttgttaata c attttagt   4560 attcacattt taaagtaatc gtctgtatta ttgatctacg agagtaaagt g ctgtgaata   4620 caaactgcta agaattttc taagcatttg ttttaaagaa gtggttcctg g tatacacta   4680 gatgtccgtt agccacttga gagtctgatg aaaactgtga gctctcttct g agagaaata   4740 cacatacatt ttgaaaattt caggggttaa aggaagattt aggatactcc c caagtatcc   4800 ttaaatctca gattaagagt ccttgtggaa gataccattg ctttgttct g tttattatt    4860 ctttgaatct ttaattttta aaatacatag tacattcaga atttaggaat a aaaaaggac   4920 agtgcagtga acattttcct tcccattcct atctcttata ctatgtacct a actcctctc   4980 cacaggcagt gattgtgact gattcttact attttttgtgt atctttccag a tattctctg   5040
```

```
catattaagc aaatgtttat gtatattgtt tcattttcgc cttttttgca c agataatag   5100 tatattatac acaaccattt tgtaccttgc tttttcagt tgatatattt t ggaatttat    5160 tcatacccat acagaaaata ctcccttatc cttttatag tgtatagttt a cactgcatg    5220 gaaatactgt aatttattaa accagttctc tagtgagggc atttggctgt t tttcatctt   5280 tccctgttag gctgcaccaa ataacctcct acacaaattt gcacgtatac c tgtcggata   5340 cgttttaga aatagctatg tgcttttgta attagataca ttttgatgaa t tgtcctcca    5400 cagagattga actaatttat gctacggcct aagaccagca cagtgagtta t agctttttt   5460 ggatctttga tcacttgata ggtgaaaatt ctactttaca tttctcctag t ttgactgag   5520 tttgaacatc tcttaaaata ttttaattat ttatatttt ttcctgctaa a tgcttgttc    5580 acttattatt cacccatttg tctgtctttt ttttttttc atctttttta c ctaccttaa    5640 ttgtaggatt tagctattta catactagag aaacctgctc tgtgtgatac a acttaaagt   5700 tatttttttc cctgtctttt accttttggc tctgctaatg gtagttttgc c atgcatttt   5760 ttttaagtag ttgaatgtat tagtctttta ggacttctag gccttatgcc t agttagaaa   5820 ggtcttcccc actcaaatta ggaagaattc tataattttt aaaatttcag c ctttacatt   5880 taaaactgtg atccttatgg aatttatcct ataaaatgtg aggtctgggc c tagccttaa   5940 cttttttcaaa aggttcactg aataattcac ttgcttcttc cagtgatttc a ggtagcttt   6000 tatataagtg aatttgtttc tggatgttct attctattcc acgtagctgc c tatcttta    6060 tgtattaatg caaaacattc ttttaatttg tcaggatcta aatgtgttac a cttattttt   6120 cagaatttcc ctggctattc ttgcttattt ttccacatgt attttagaat c agcttattc   6180 taagaaaaag cctgttagca ttttattag gtccgttcgg cctagaaaga c ttgacatca   6240 ttatgatgtt gactcttact aaccaagaac atgcagtatt cttttctgt t ttcctataa    6300 ggtatcttaa gttttcattt ttatcttgag atttaaaag tttttttcta g gtattttat    6360 cttttctgtt gccattgtaa atgggtcttc cttttcccat gttttgttt g tgttataga    6420 tgaaaacaga gctattgctt tctctttgga cctacttcct tattgaattc t tttatttt    6480 agtagcactt tatcatatta tttgtaaata gattatgatg ctttcttttt a atgtttcaa   6540 catttttttc tctttcttct ctaattgcat tggctagtgc ttccagaaca g tgttcactt   6600 acagaattag ggtcttagta gacatccttt tctgtttctg atcttagttg g aatgcttct   6660 aatgattcca cattaatcat agtgctgact ctttaactga aataaatgta t gttgtcaca   6720 tattgaggat ttttattga gttttatatt gatttttaa atgggtgttg a atttagttg    6780 aatgccttct tggtgtctat ggatacgatc atgtatttat gggttttcat c catactcat   6840 gagtgagatg gttattgatg agcttttcag ctgaacagct acaccgtggt a tataccaag   6900 ggatcttagg cattttttacc gtgtatactc tgtactatgg aaaccttgtc t ctctgatgt   6960 ttactgctct atcctagctt ctagaacagt gctgacacat gaaacgtgtg t ggtattttt   7020 tcttttaat gatttagtaa gttaagttag taagtttgga tcttagattt a acatctaat    7080 atctttctaa gtcagcaaat ttggggagtg tgattcttgg catttcaaaa g gattttgt    7140 tttctttatg acagtattta tcaagagttc ttttacataa tacatcttaa t aaatttaa    7200 gtatagattt atgggtaaaa taactcgctt aagtaaaata attcacactg t actttaaag   7260 ccttctgtat gtgtgcacta tgctcaatat ggtgatatga acctaagttc c agtctttac   7320 taagtagaaa atatgggcaa agtattaaac cccataatgc cataataaag g tacagagtg   7380 ctgttctagg caagacataa tcatcatgct cctttctgtc acctaaacaa g aaagcaagg   7440
```

```
atccacttaa actttctctc gaatttctag ttagtgtctg tggaatttca t aaactgaga    7500 gttcaggagg agaaatctta cattgtactg agaaatgaac ccttaatgcc t ttctccttt    7560 aaaatgtttt gactagttca gcctttgata ttttatcaca ttgctttgag g cattgtaga    7620 ctgttttaat gcttgagaat ttctgaaact cctaataata tcacacttca a ataatttca    7680 ggagatccat ctccttaact tgtaaaccat aacagtactg gaaatttaga a gtatgagaa    7740 aagaagaaaa taaattattc aagcctattt atcttacaca tcttttatca a ctatgtata    7800 gggctttcca gtctttttc atgtttatgg ttttaatcat tatatgtcct g tttactttt    7860 cactccaaac attgtatcat gcttttcttt tttctttct tttttttttt t tttttggc    7920 attcctacct catgtgttta aaaagaaaa aaatgcaaac tgaggcttgg a aagactgga    7980 ctgatcacct agctattata catgtgaatt cctacaaatg aaaatgcccg a atactagaa    8040 aacgtggtac tgtgtaaata gtattgattc aagtattagg gtgatgacac a gatcagatt    8100 gtgggaataa atattgtac agctgtacag agaaagattt tgttcatgag t ttcagcaat    8160 gcaaagtaca tatttagtta taaattctaa ataaatagtc gattttgtt t acctgtcat    8220 tttattattt caatatatac ttttcttctt ttgataaaat tcctgaatta a aaatatatc    8280 catatctaag gcagagttat gatcatagca gttacttgta ataatttatt a atggtgttc    8340 aagtatagat ggcacccata tctcctgcta ttgatttttt taagtaaaac t ttaaatgac    8400 aggtttatat tttaatgtat gccttaagca tcttaattat cttatcagag t taaggcatt    8460 ttgagaatat ttttgcaata ccagccatat attcttcatt ttcttccact a aaatatcat    8520 cagattcact tttttttta aactgtactt tgttttaac ttcttggttg a ggtcagcag    8580 catgctgcat ttatataata gtaatattaa aattgtaaat ttttttttaa a gttacactt    8640 caaaaattaa aggggaaaaa gtatttcaag tcagagggtt tatcacaaag t ttttctagg    8700 tctgttttat agcagtgaaa caggtatgcc aagttgttaa taaatgggca t gcattgctc    8760 ttaaattctt aaaattaaac ttgatcagtt gtgagggaca gcttatgtct a tgcattgcc    8820 taaaaattgt ttctgtttgt tggctttact tatagaaaat cttgatttt t tttcattac    8880 ttgatatttt tattctttgt ttttcctgat aagctgccaa atggtgtcac t taccacact    8940 ggaacatatc aagaccggtt aacaaagcta caggataatc ttcgccaact t tcagttctc    9000 ttcaggaagc tgagattggt atatgacaaa tgcaatgaaa actgtggtgg g atggatccc    9060 attccagtcg aggtaatttt ttgtgataga gggaggatga atataaggtg t gaactagtg    9120 tcaagacagt tgttaatctt ttttcctctct ctcctgtttt agcaatattt c caggtttcg    9180 aatttttattg gttttacttt tgaccagaga agatgaaaat gtgatatata t gcataaaat    9240 actactatat ttttacatta acaatttctt gtagactttg acaggcttat a gtaatttt    9300 gttgttgtta ggaagaaatg ttttcctatg gcaattttta ttgctgtcag t gtctccttt    9360 taattaagtc agggatattt ttagtaggaa ttttaatagt atcatatact t ttaaggtgg    9420 ttttcatgaa gtactttaca gataaaatat tatttttatt attattaatt t ggattttat    9480 atttagccca gtggaatcac tatatttaa aaatatattc tctaaattta a tcttgggtc    9540 atacctatt agtaattag gcatatattt ctataagtca cccttcctg t tgacaaatt    9600 atatctctgc caccaaagga agctggtaag agatgaccag agaaaaatta a actgcaaaa    9660 atgcctaaaa agaagggtc agagatgtgg gagaaagatc agaaatgtgg c ctacatcgt    9720 cagatgctac agagaagtca gggaaaataa ggaatgaaaa ctgtccagta g attttgcta    9780
```

-continued

```
gatgaaaatt gttggtatat ttgagtagag cttcagtgaa atgatagcag c gtgaagtct    9840
gatcctagtc gggtgaagat taaacaggaa ataagaagct ggagccggca a gtggatatc    9900
agtcttcaa gaagctttga aaaaaataag agaggaaagc agtagatgga a ggagagatg    9960
gaatcgaagg tttgcaggag gaagaggagc ttccctccaa atagaagaga t aggaacatg   10020
tttgaataat aaaggaagaa agctgtaggg agaggttgag agaaaggtgt a taaataatg   10080
aagacaggag ggcagagtaa tcagggcaca ggaatggaga ctaatcgtct t caggaggaa   10140
ggacagctct gcattgagac agatgaaaga aagaaaagga gaatgtagac a tgggtgagt   10200
ttatatatat cccaagaatt tgaagaagtt ttatcaggtg aatcctagtt t taccagtca   10260
tttaccttta gcctattctt gcattggtaa tacacgatgg taaaggctag g tgattcctg   10320
aagtctgcca cacttatgcg gtaaattcca tcactaacca tgcatactta a ttacgattc   10380
tgctagaagt ttcattgcta tataaatttg tttctcctac aaagaaaaag t tctcacaac   10440
tgcgaaaact taagacatct agaagtttgc atagactctg aagttttaga t tgcaagtta   10500
atgacaatta tataatacag atccgtgaag ttcttttctt tttattgcag a tgaaggaaa   10560
gcctgtttta tctatctcaa tagactacaa atctcttagg ggcaggaatc a catcttgtt   10620
tggcattact tttatagtgt ttcataatta aatatttgct gattgagtag g gtttttta   10680
aattttatt ttattttatt ttattttta cttctcccat cttcctgctg g aagtattgt   10740
ttagttgtac atgacaacca atgttataaa ggctgttttg caaagaaac c tgaagggt   10800
aatgcataga atgcattgaa atggtcaact attaaagctc ttatttcagg c catcacctg   10860
aattgaaatt attttatac aaataaaagt ataaaaattg accttaatct g atatattct   10920
ctatacaagt gattagaaaa cttgaattat attttttgcct tttaattttt g ttaatcatt   10980
cccagcaact tattccatat gtggaagaag atggctcaaa gaatgatgat c gggctggcc   11040
cacctcgttt tgctagtgaa gagaggcgag aaattgctga agtaaataaa g tgagttgtt   11100
agttttaca ttttatgttt tagagttatt gataaaaatt actagggagt c tgatgtaac   11160
tccaaaacat aatttgaatt atcaaattac atgaagttgt ttctgcggca a acttcacct   11220
atttagaata cagccaagaa atgaaaggta agcagaaatg ctgtctgaat a gtcagaaga   11280
gaaattgcaa aattcattcg ataaagctct tagaagagct ccttagacac t tagtcacaa   11340
tccatttact ttttctttt ctgggcagaa ttctaccttt ctagcttata g catatttgg   11400
agcagcaaat gataaaaatt tacaaatatg aaatgtgaat gtctcaacac c tgaataaaa   11460
aatttagaga actatcccag cattattatc tactccaacc ccacaaaaag c ttgtaactg   11520
gaatgtattt atcgctgaat actttcaaaa gttcagaaga taatgttcaa a tagttctcg   11580
tgaaacagag agaaataggg aaaggtgtca gttcattctg gggatggaaa t gtggcccca   11640
gcttagcaaa acctaccaga gatagcacag tgaataaaac tttcagcatc a ctctttcac   11700
tgacaaatat agattgcccc ttcctgaaat tcttaattct aattaataga a ctcatcagt   11760
gtattaataa tccaccactg ccaaagagag tcttctgagg tatatgaaga t tttatagtt   11820
cagtttgtat gtataataca tgatgtcagt aaactacctt gaaaaaagat t ttctcacat   11880
gtctaaaaga catctgataa aattcaatac tgttgctgat tcaaaggaca c ttaaaacta   11940
ttagcaagac agtgtgtttt ttttttaaat ctttttcttt tagataaata c ccaacattt   12000
ttcataaggt gaaatataga aatatcctta ttaaaaacaa gcatgaaata a gatacttta   12060
taacactatg tttaatatta ttttagaagt tatagccagt acaaaaagac a gtggacaaa   12120
tgacagttgg gaaacaggag ttactatgta tgagcttgtt agaatggtca a agaaactca   12180
```

-continued

```
actgatgaac aactagtcta taagagttcc gtaaaagggt ctaagacaag a ctgatacca   12240
tgctcttaca atgctgtaaa cctattagat tataagattc tattgactct t gtaacaatt   12300
aatattaagt agataggaat tatgtcaata atgtgtatga ataaacttat t aagatacat   12360
aaaggaagct ttgaatgatt aaaagaacat ataaagttct tggatgagca a tacatatta   12420
taaaaatacc agtcttgatt taatactcac agttttaata cagtaacaat c caaatccta   12480
ataagaaagc atgcaaaaac aataggattt tagtgcaata ccaatcaata a acaaatcca   12540
aataaaaccc aaatggaatt tttttcttga agtatacaa aaatatcaaa g aaaatgttg   12600
ataaatacga ctaataaagc agaattctta gcttcaaaaa ttaaactgta a tatgaagca   12660
tattataaaa atggtaatta ggtgtataat actggcacaa gaataggcag a ttagtaaaa   12720
taatctagcc agaaaaacag ccttcttatt gtacatgaga atttaatatg a cagaagagg   12780
gcttgtgtgg aaaattagtc tttagaaata gaaactttgg gggcgaaatt a agctagctt   12840
ttacattaca ccataaatca aaatgaattt cagagttgaa ataagacct g caaaacaaa   12900
atattggata atttttttaag tattttaaaa ctcggaagaa aggaaaaaga t ggatagatt   12960
ttataaaata aaattttgta acttttttaa aaggtgaaac acacatttag a aaactattt   13020
ccaaaaaatc tgattgtaat acatgacaat cataataaaa aactcacagt a aaaaattgg   13080
tagagggtga ggaggagaat gggaactttt agtttagatc ttgaaaaata a ctggtgttt   13140
ggtagtctag atgtatgaga cattcactta ttaagacgtg ttatatgttt c tgttgataa   13200
atatgtatta ccctcaataaa tgtgttctgc ttatgtttct ctaatgattt t tttataaaa   13260
tataatgaaa tatgtatata aataaaacac cattataata ataactttgg t ttcagagta   13320
ccacatgtgt aactaatgta aacatagttt gttctgtacc atagaggatt t tataatatt   13380
ttgtaaaaaa taaagctgtg taaattcaga aagatacttt ttctatattt a catttctct   13440
tcaattttca ttaagtttct ctttttttccc aatttgataa ctcagaaata a catgtctttt   13500
gacttttaaa agttctcttt tataatcaaa atatggtaat tctttggcag c atgtaacca   13560
aaaaaaaaaa tcttactatc tactgacata gagttttgtg gattttaagt a aaggatata   13620
attgaaacaa ggatatgatg tataaaagga cttctttctc cccatgagga t ttagctccc   13680
tacagcctct ctctcctgga cccacctaca taattgtttc cctcaaacct t tcagtgcac   13740
ttatatcata tttggggttc agtaaataat ctgtatcata taattatggc t tcataagta   13800
ttgtttattg ctaagccgca tagtatacta gggtcatatt tccttgattg a ataattttt   13860
tgttttctg aagttaattc ttacctcttt aattttctaa aattttagtt a gttttttat   13920
gcatctatga caacatctca gtactatttt ccaattttcc acagtcagaa t catcagaca   13980
gtttcatggt tctcatccca ccctcccaag ttttctatgg tcttataggt c tggatggaa   14040
tgctggctag gcctgctttt cagctctggg gctttccttc acctcttctg t tggtttcac   14100
tatttcttca gctcatgtct tcccttttct tggttttctt ccttgttggt g atgtgcata   14160
catcagtgac ttcttagaa ggaatgcaga cacttaaatt ttgagtcctt a catatttgt   14220
ccagttgata gtttggctgg ctataaaatt ctatgttgta agttatgttt c ctcagaaat   14280
ttgaaggcat tccataatct agtataggt ttggcagact ttttgtttaa a ctactagat   14340
agtcaatctt ttaaccattc ctccagtttt cattcccagg gctcacctgg t gcctctgag   14400
atggtctctg tctgtggttc tccatggtgg atcaggcgta ttctcggtgg c atccctctt   14460
gcatgcccag gccttctctg agtcactgac cactccctct ttacttttca t ctgaaaatt   14520
```

-continued

```
taccttgcat ctgctgttgt gtcctttctg atcacttttc tctgcatcag t ttatagctt    14580 ttttttattcc tctcctgcca cacactcaat agatacacaa tgtttctgaa a gtttgtgta   14640 tatttacgga atgaaagtat tttaaatttt ttcccccatt tttacttctg a cattgagat    14700 ctcttccttt gattaaatga cttggatctg ttctaagtgc ttttaacttc a ggataaaac   14760 atgttttagt taacgtgata tcaaactgat gggttattac aaagagaaaa g aatcagttt   14820 aggtgtttta aatgaaccag gtttaaagct aaactctatt tctgtgggaa t tgcttttta   14880 aaagacaatt tagaggtaaa gtaccttctt gagtatcatg gggaagaact c atttgatga   14940 cctcataact ctctttgtat gaattcttct acctatattt tgagaaagca c tgaaagatt   15000 aggtggtggg cacagggaaa agatgggaga gggctaacat ttggttaact t aaatttaaa   15060 tcccaaataa ggaagaagaa aataaaatta actgctaaaa ggcaaacaaa t tgttttttt   15120 tttttttttt taccaaaagg cttttttaat tcattcctta aaaaaatata t aaatgtgaa   15180 ttaaatgtag catattctgt tactagaata atcttaccta cagttaaccc t agctactga   15240 catagagttt tgtggatttt aagtaaagga taaattgat acaaggatat g atgtataaa    15300 aggactttct ccatatgagg atttagctct ctacagcctc tctctcctgg a cccacctac   15360 ataattgttt ccctcaaaca atttttatttt attatttttcc tcaacttctt t aagctctgt  15420 gtctccattc tagaatataa gattaaaata tatgattaaa agttttaatt t ttaaaatac   15480 tgagctcgtg atccattgat actttttttt tttttttttt tttgagagac a aaatctctc   15540 tctgtcaccc aggctggagt gcagtggcac gatctcggct cactgggttc a gcaattct    15600 cctgcctcag tctcctgagt agctggggtt acaggcgtgc accaccatgc c cggctaatt   15660 ttttttgtgtt tttagtagag atggggtttc accatgttgg tcaggctggt c tcaaactcc  15720 tgacgtcgtg atcacctgcc tcggcctccc aaagtgctgg gattacgggc g tgagctact   15780 gcacccagcc gatacatctt ttttttttc cgtaatggca cacacacccg a gggtgtttc   15840 tcgtagtgaa aactggctat agatgataat gtactgattt gattatttaa t cacatagat   15900 gctattaaaa ataaagttca ctgatttgat ttgaccacta tttataaata g ctacattca   15960 taaacttaag ttttttgtctc tgtcaattat gttaatccac attcttatgt a aatataggt  16020 ttgctttttt tttagttcat gcatttacta ggtgatagag ttttaaagtt c acggaatct   16080 tagctggtaa cactaaaaca ttgaaaatac atcttaccta ttatggtatg g agtataaaa   16140 tgcatagttt ttaataatgg ccattattaa atgtcttttt tttttatact g aggagttat   16200 ttaaacaaaa ataagttttg aaatgattgg caataatttt tgtttgcttg c ttattttttt  16260 ttccattctt gtaggttttg ggagaagctt tttgatttgg cttttgtttat t tttcttca   16320 aacatgaaaa tatttaaata tttgtgtgcc tgctctctga caggcattgt c ctcagtacc   16380 agaatttctt ccatgaagca gctggatgtg ttgtcggcta tatctcatt t cacatgagt    16440 ggacaagttt cttcttggag aacataagac tccagtggaa acaaagcagc a cctgtttca   16500 tgtacccatt tcatgttttg atgaatattt acagaaacaa aagtattgtg c catatttt    16560 aatacattgg catttggttg tattaaataa gttgctttat agatctgtgt a atttataat   16620 aaaattatat tatttgcatt caattaaaaa gtcagaattt tattacaatg a atattttct   16680 ttctttctaa ataagctacc taaaataagt agatttatat accctcagc t gaccctcag    16740 tcattttcaa gatattatca tatcattgtg tacttgaaat tgtgcagaag a acatattga   16800 tggtgtgttt actatttagt cgttatgtc tgtctggtttc ctaacaatac a aaaaccacc   16860 aataactatc ctggtgctat gaacttttga ggcacatgat ttgtagtcag t atttgatgt   16920
```

```
aaatcatcat aagacaatat ggctggtttt aatagtcaaa ttcgtggttt a tttaaatac  16980 ttttcatttt ctcttaatat atcctggaat ccttaagcca aatacccatt t aaaggatgg  17040 acacttgttt gagaccatat gctttaggtg caggggtgtc aatcttttg g cttccctgg   17100 gccacattgt aagaagaaga attgttttgg gccacatata aactatacta a cattaatga  17160 tagctgagaa gccaaaatat aaaaaaatca cgaaaaacat ctcataatgt t ttaagaaag  17220 cttacaaatt tgtattgggc tgcactcaca gccgactggg gccacattgc c tgtgggcca  17280 cagttggaca agcttgcttt ggggacatca gaatgagttt tattttgctt a acgctcttt  17340 tcttgatggt aaaatgaaat tgaaaagat agtaggtagt atttacaagg t tggcattga   17400 gtccatgcat ttagaaagta aaccattttt tgtcaagtgt cacagctttt g tgtgaatat  17460 tacattacat ggtatcagtt agcatcaact tttttaagt atttagtcta c ttacacatt   17520 cgcctgttaa tgtacaaaat tgggcacagc tgatggattt tgaaaatagc a gctgtcaac  17580 gtctgttaaa atcaatcagt ggcaagactg tgtatattaa atcctatatc g tgtcatgaa  17640 aatttattta cactttagcc tctaataagc ataagtgtca gctttgctgt t gatcatttt  17700 catgacatgt tttgactctg gatattttat ttgtatgcta atttttttaa t ttaaaactt  17760 tgtggcatct ttgagaaacg ctatcccaag agccttataa tatattaatt a tttaaaaat  17820 tttctattcc ccagtgttga atattatctt gaaataccc tacaaatttt a gttgttact   17880 tttttaaaaa acaattacga ggcttaaata aaaagagta ccagaatgta t atttccaaa   17940 tgaggattct tgagagtagt cttattggta ggttatgcat ttatttcagt g gtgagacca  18000 ttgtgatagc cagctgcaag ccctgagttg atactgatta taaagtctgt t tttaaccac  18060 ccagatgacc aattgtcatc ttatgtatgg gtatgcagaa agtacaactg g cagagacct  18120 tagattttat aatccaatta cataaatgag aaaaccaaga agaaggaatt t atctaagat  18180 caaataccaa gttagaggca agttggaac tgggaccgag attgccagcc t cccaatata   18240 gcactttat attcctctgt tttgctgcta ctcttgattg ctggcagaag t gttggtttc   18300 ttggtctctg tgatgaaaaa gactttatag gcttggttat tcttcatctt t cccagcaat  18360 ttgaatcaat tttgttagat atatacaacc acttaaataa cagactatca c ttacttatg  18420 ataacagaat atagaagatg ggtcatctga aaacttgtgc aagggagact a actaaaaat  18480 accagcagtt tttgtttccc gaagactgtg ttaaagtgag ctttagagtc g agccctgtg  18540 tactgtatag tcctgttttt ctctgactgc attgtgctag ttctctttc a aatgtgaat   18600 taaattcagt tatgaaagat tattaaagtc tctgtaaatt gattttctat t ttctaataa  18660 gagtttcttg gtctttcctt ttagccacct atttcttgtt acttccctaa c tctgaatag  18720 aagcaataca agcaacttca ttttagtttg ttttttaatg aaatcaaaag t aagattgtt  18780 aggcctcttt ttaataagca tacaccaatt tatctggagg tagtttaata t agtgtctta  18840 aaattaatta agtatattat ctccaaatgt aatgtttcca aggggttatt g aataataat  18900 aattattgtt attataacta gtaaacactc tgaccagaag ttctctattt c tatcttgtt  18960 ttatctaagc agacatttac cacataggat ttgaagaaag aatggttaaa a agaagtcta  19020 caaatcttag tcaagtagaa tccagtgta gagatacaga gacacatgcc g tgcacattt   19080 caggcattca gcaaatctta gtagagaaga ttgcattggg tactctgcca t tgtcttca   19140 gttttttagaa ttgaaggag attgcaattc atgctatagg caaacagtga t ttctgccgc  19200 acttttgaaa gactgattgc atgaggcatt gtacttttat tatattttct a tatcgacag  19260
```

```
                                                  -continued
tttacatttt gtgcctaaca gtaacatttg ttgaatgttt acttatgtgt c aggcacaat  19320 tctaatactt gacatgaatc agaccattta atcttcataa cagctcttat g aggtagttt  19380 caattattat ttccattttt ctgatgtgga aactaaagta ccgggaggtt a aataattag  19440 gtcagtgttg taagtttcat agtgaaggat ctggccgggt gtgatggctc a tgcctgtaa  19500 tcccagcact ttgggaggcc aagacgggca gatcacttga agtcaggaga c cagcctggc  19560 caacatggca aaacctcctc tctactaaaa atacaaaaaa actagatggg t gtggtggct  19620 ggagcctgta attctagcta ctcaggaggc tgaagcagga gaatcgctga a acccaggag  19680 gctgagattg cagtgagcca agattgcgcc actgcactgc agcctgggaa a aaaaaaaaa  19740 aattcgtagt gaaggatctg aatgacttcc agagatctgg ctctagagta t gggctcttg  19800 accgttaggt tatgctgccc cttagaaaac ttatatgctt atgttttata a caaataaat  19860 gtttagctga tttattgatt tgtttatggt ggaagtggaa gagtaagcag g gcctgggc   19920 cggggctggg gccatagacc tctgcaggct ggattttttag aattcaggat c cctgtcagc  19980 aaatatttaa ggccagaaga gggttgagac catctgcctt atagggttat t tagcttaat  20040 ttctgtctgt atcattataa tcctaactta tgatatttta atcttctaac t tcatggtct  20100 atatttcctg aaacatttt gataaattct tttgtttcta cagaaactca a acagaagaa  20160 tcaacagctg aaacaaatta tggatcaatt acgaaatctc atctgggata t aaatgccat  20220 gttggcaatg aggaactaag ctgatattta aatttcctgc tttacacatg t tataccatt  20280 gttttttccc tcaagtattt tttccctgtg aagaagatta tttatctgct t ttattttag  20340 tcactaaaac taaagtttt atttttacat tgtgattttt acattaaaat a ttaactttt  20400 ttaatgctat tttatgaaag attattgtaa taaactttga tggggtttgt a ttttggtta  20460 atcttcatga attgaataat tgttttttta aagcaaaata aagtttttta a ataaatgtt  20520 aatatttgat taatggattt actcattcca attacccttt tagaagaaaa a tatttaaat  20580 atttctgcag ataaaagt                                                205 98
```

HELICAL CYTOKINE ZALPHA33

CROSS-REFERENCE TO RELATED APPLICATION

This application claims the benefit under 35 U.S.C. §119 (e) of provisional application No. 60/139,121, filed Jun. 14, 1999.

BACKGROUND OF THE INVENTION

Cytokines are polypeptide hormones that are produced by a cell and affect the growth or metabolism of that cell or another cell. In multicellular animals, cytokines control cell growth, migration, differentiation, and maturation. Cytokines play a role in both normal development and pathogenesis, including the development of solid tumors.

Cytokines are physicochemically diverse, ranging in size from 5 kDa (TGF-α) to 140 kDa (Mullerian-inhibiting substance). They include single polypeptide chains, as well as disulfide-linked homodimers and heterodimers.

Cytokines influence cellular events by binding to cell-surface receptors. Binding initiates a chain of signalling events within the cell, which ultimately results in phenotypic changes such as cell division, protease production, cell migration, expression of cell surface proteins, and production of additional growth factors.

Cell differentiation and maturation are also under control of cytokines. For example, the hematopoietic factors erythropoietin, thrombopoietin, and G-CSF stimulate the production of erythrocytes, platelets, and neutrophils, respectively, from precursor cells in the bone marrow. Development of mature cells from pluripotent progenitors may require the presence of a plurality of factors.

The role of cytokines in controlling cellular processes makes them likely candidates and targets for therapeutic intervention; indeed, a number of cytokines have been approved for clinical use. Interferon-alpha (IFN-α), for example, is used in the treatment of hairy cell leukemia, chronic myeloid leukemia, Kaposi's sarcoma, condylomata acuminata, chronic hepatitis C, and chronic hepatitis B (Aggarwal and Puri, "Common and Uncommon Features of Cytokines and Cytokine Receptors: An Overview", in Aggarwal and Puri, eds., *Human Cytokines: Their Role in Disease and Therapy*, Blackwell Science, Cambridge, Mass., 1995, 3–24). Platelet-derived growth factor (PDGF) has been approved in the United States and other countries for the treatment of dermal ulcers in diabetic patients. The hematopoietic cytokine erythropoietin has been developed for the treatment of anemias (e.g., EP 613,683). G-CSF, GM-CSF, IFN-β, IFN-γ, and IL-2 have also been approved for use in humans (Aggarwal and Puri, ibid.). Experimental evidence supports additional therapeutic uses of cytokines and their inhibitors. Inhibition of PDGF receptor activity has been shown to reduce intimal hyperplasia in injured baboon arteries (Giese et al., Restenosis Summit VIII, Poster Session #23, 1996; U.S. Pat. No. 5,620,687). Vascular endothelial growth factors (VEGFs) have been shown to promote the growth of blood vessels in ischemic limbs (Isner et al., *The Lancet* 348:370–374, 1996), and have been proposed for use as wound-healing agents, for treatment of periodontal disease, for promoting endothelialization in vascular graft surgery, and for promoting collateral circulation following myocardial infarction (WIPO Publication No. WO 95/24473; U.S. Pat. No. 5,219,739). A soluble VEGF receptor (soluble flt-1) has been found to block binding of VEGF to cell-surface receptors and to inhibit the growth of vascular tissue in vitro (*Biotechnology News* 16(17):5–6, 1996). Experimental evidence suggests that inhibition of angiogenesis may be used to block tumor development (*Biotechnology News*, Nov. 13, 1997) and that angiogenesis is an early indicator of cervical cancer (*Br. J Cancer* 76:1410–1415, 1997). More recently, thrombopoietin has been shown to stimulate the production of platelets in vivo (Kaushansky et al., *Nature* 369:568–571, 1994) and has been the subject of several clinical trials (reviewed by von dem Borne et al., *Baillière's Clin. Haematol.* 11:427–445, 1998).

In view of the proven clinical utility of cytokines, there is a need in the art for additional such molecules for use as both therapeutic agents and research tools and reagents. Cytokines are used in the laboratory to study developmental processes, and in laboratory and industry settings as components of cell culture media.

SUMMARY OF THE INVENTION

It is an object of the present invention to provide novel polypeptides, polynucleotides encoding them, and methods of making them.

It is another object of the invention to provide compositions and methods for modulating the proliferation, differentiation, migration, and metabolism of responsive cell types and for regulating tissue development.

Within one aspect of the invention there is provided an isolated polypeptide comprising at least nine contiguous amino acid residues of SEQ ID NO:2 or SEQ ID NO:4. Within one embodiment, the polypeptide has from 15 to 1500 amino acid residues. Within another embodiment, the polypeptide comprises at least nine contiguous amino acid residues of SEQ ID NO:2 or SEQ ID NO:4 operably linked via a peptide bond or polypeptide linker to a second polypeptide selected from the group consisting of maltose binding protein, an immunoglobulin constant region, a polyhistidine tag, and a peptide as shown in SEQ ID NO:7. Within further embodiments, the polypeptide comprises at least 30 contiguous residues of SEQ ID NO:2 or SEQ ID NO:4. Within other embodiments, the polypeptide comprises residues 41–55 of SEQ ID NO:2, residues 56–77 of SEQ ID NO:2, residues 78–92 of SEQ 1) NO:2, residues 78–92 of SEQ ID NO:4, residues 93–110 of SEQ ID NO:2, residues 111–125 of SEQ ID NO:2, residues 111–125 of SEQ ID NO:4, residues 126–148 of SEQ ID NO:2, residues 126–148 of SEQ ID NO:4, or residues 149–163 of SEQ ID NO:2. Within additional embodiments, the polypeptide comprises residues 41–163 of SEQ ID NO:2, SEQ ID NO:4, or SEQ ID NO:5; residues 34–163 of SEQ ID NO:2, SEQ ID NO:4, or SEQ ID NO:5; residues 34–178 of SEQ ID NO:2, SEQ ID NO:4, or SEQ ID NO:5; or residues 18–178 of SEQ ID NO: 2, SEQ ID NO:4, or SEQ ID NO:5.

Within a second aspect of the invention there is provided an expression vector comprising the following operably linked elements: a transcription promoter, a DNA segment encoding a polypeptide as disclosed above, and a transcription terminator. Within one embodiment, the DNA segment comprises nucleotides 52 to 534 of SEQ ID NO:6. Within another embodiment, the expression vector further comprises a secretory signal sequence operably linked to the DNA segment.

Within a third aspect, the invention provides a cultured cell into which has been introduced an expression vector as disclosed above, wherein the cell expresses the DNA segment. The cell can be used within a method of making a polypeptide, the method comprising culturing the cell under conditions whereby the DNA segment is expressed and the polypeptide is produced, and recovering the polypeptide. Within one embodiment, the expression vector further comprises a secretory signal sequence operably linked to the DNA segment, and the polypeptide is secreted by the cell and recovered from a medium in which the cell is cultured.

Within a further aspect of the invention there is provided a polypeptide produced by the method disclosed above.

Within another aspect, the invention provides an antibody that specifically binds to the polypeptide disclosed above.

Within an additional aspect, the invention provides a method of detecting, in a test sample, the presence of an antagonist of zalpha33 activity. The method comprises the steps of (a) culturing a cell that is responsive to zalpha33; (b) exposing the cell to a zalpha33 polypeptide in the presence and absence of a test sample; (c) comparing levels of response to the zalpha33 polypeptide, in the presence and absence of the test sample, by a biological or biochemical assay; and (d) determining from the comparison the presence of an antagonist of zalpha33 activity in the test sample.

These and other aspects of the invention will become evident upon reference to the following detailed description of the invention.

BRIEF DESCRIPTION OF THE DRAWINGS

FIG. 2 shows an alignment of representative human (SEQ ID NO:2) and mouse (SEQ ID NO:4) zalpha33 polypeptides.

DETAILED DESCRIPTION OF THE INVENTION

Figure 1A:
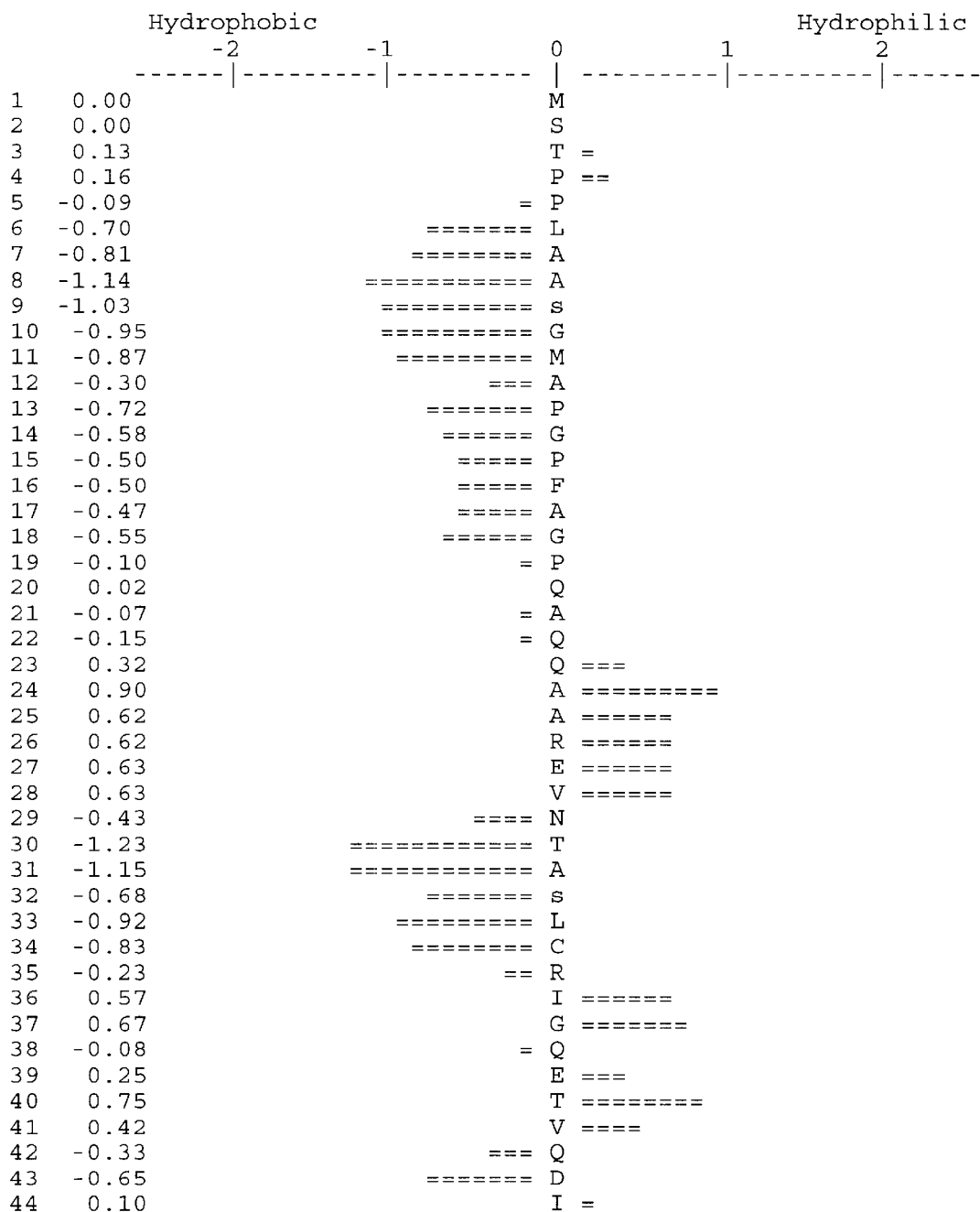
FIG. 1 is a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

Prior to setting forth the invention in detail, it may be helpful to the understanding thereof to define the following terms:

The term "affinity tag" is used herein to denote a polypeptide segment that can be attached to a second polypeptide to provide for purification of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (*Grussenmeyer et al., Proc. Natl. Acad. Sci. USA* 82:7952–4, 1985) (SEQ ID NO:7), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; Eastman Kodak, New Haven, Conn.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

The term "corresponding to", when applied to positions of amino acid residues in sequences, means corresponding positions in a plurality of sequences when the sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. The isolated polypeptide or protein may be substantially free of other polypeptides or proteins, particularly those of animal origin. An isolated polypeptide or protein may be provided in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function (s) of the sequences are retained.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end.

Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides novel cytokine polypeptides and proteins. This novel cytokine, termed "zalpha33", was identified by the presence of polypeptide and polynucleotide features characteristic of four-helix-bundle cytokines (e.g., erythropoietin, thrombopoietin, G-CSF, IL-2, IL-4, leptin, and growth hormone). Analysis of the amino acid sequence shown in SEQ ID NO:2 indicates the presence of four amphipathic, alpha-helical regions. These regions include at least amino acid residues 41 through 55 (helix A), 78 through 92 (helix B), 111 through 125 (helix C), and 149 through 163 (helix D). Within these helical regions, residues that are expected to lie within the core of the four-helix bundle occur at positions 41, 44, 45, 48, 51, 52, 55, 78, 81, 82, 85, 88, 89, 92, 111, 114, 115, 118, 121, 122, 125, 149, 152, 153, 156, 159, 160, and 163 of SEQ ID NO:2. Residues 42, 43, 46, 47, 49, 50, 53, 54, 79, 80, 83, 84, 86, 87, 90, 91, 112, 113, 116, 117, 119, 120, 123, 124, 150, 151, 154, 155, 157, 158, 161, and 162 are expected to lie on the exposed surface of the bundle. Inter-helix loops comprise approximately residues 56 through 77 (loop A–B), 93 through 110 (loop B–C), and 126 through 148 (loop C–D). The human zalpha33 cDNA (SEQ ID NO:1) encodes a polypeptide of 178 amino acid residues. While not wishing to be bound by theory, this sequence is predicted to include a secretory peptide of 17 residues. Cleavage after residue 17 will result in a mature polypeptide (residues 18–178 of SEQ ID NO:2) having a calculated molecular weight (exclusive of glycosylation) of 18,655 Da. Those skilled in the art will recognize, however, that some cytokines (e.g., endothelial cell growth factor, basic FGF, and IL-1β) do not comprise conventional secretory peptides and are secreted by a mechanism that is not understood. The cDNA also includes a clear polyadenylation signal, as well as two message instability motifs (ATTTA) in the 3'-untranslated region beginnning at nucleotides 679 and 753. These message instability motifs are characteristic of cytokine genes (see, e.g., Shaw and Kamen, *Cell* 46:659–667, 1986).

Those skilled in the art will recognize that predicted domain boundaries are somewhat imprecise and may vary by up to ±5 amino acid residues.

Polypeptides of the present invention comprise at least 6, at least 9, or at least 15 contiguous amino acid residues of SEQ ID NO:2. Within certain embodiments of the invention, the polypeptides comprise 20, 30, 40, 50, 100, or more contiguous residues of SEQ ID NO:2, up to the entire predicted mature polypeptide (residues 18 to 178 of SEQ ID NO:2) or the primary translation product (residues 1 to 178 of SEQ ID NO:2). As disclosed in more detail below, these polypeptides can further comprise additional, non-zalpha33, polypeptide sequence(s). Corresponding mouse zalpha33 polypeptides (see SEQ ID NO:4) are also provided by the invention.

Within the polypeptides of the present invention are polypeptides that comprise an epitope-bearing portion of a protein as shown in SEQ ID NO:2 or SEQ ID NO:4. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983.

Antibodies that recognize short, linear epitopes are particularly useful in analytic and diagnostic applications that employ denatured protein, such as Western blotting (Tobin, *Proc. Natl. Acad. Sci. USA* 76:4350–4356, 1979), or in the analysis of fixed cells or tissue samples. Antibodies to linear epitopes are also useful for detecting fragments of zalpha33, such as might occur in body fluids or cell culture media.

Figure 1B:
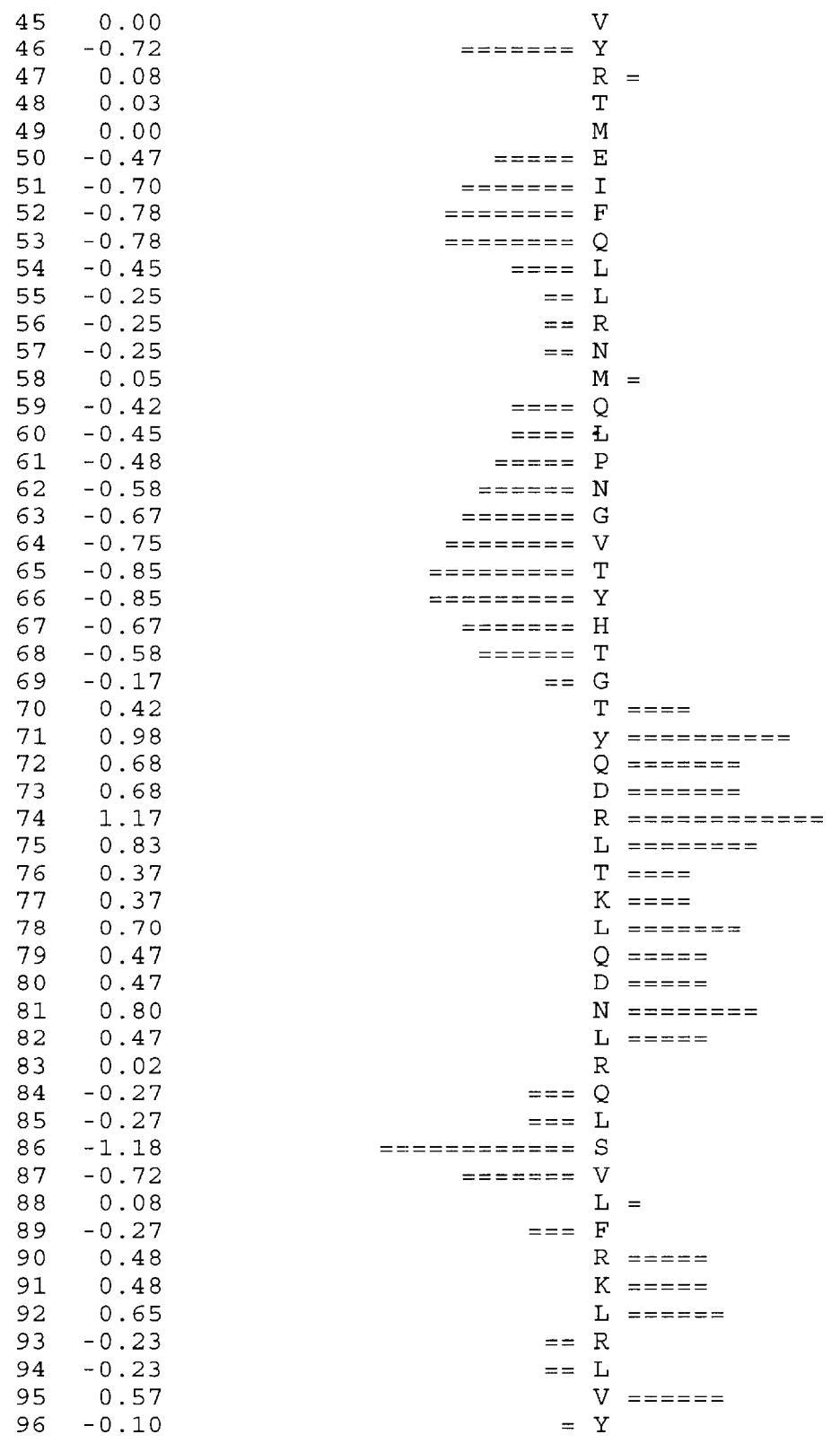
Figure 1C:
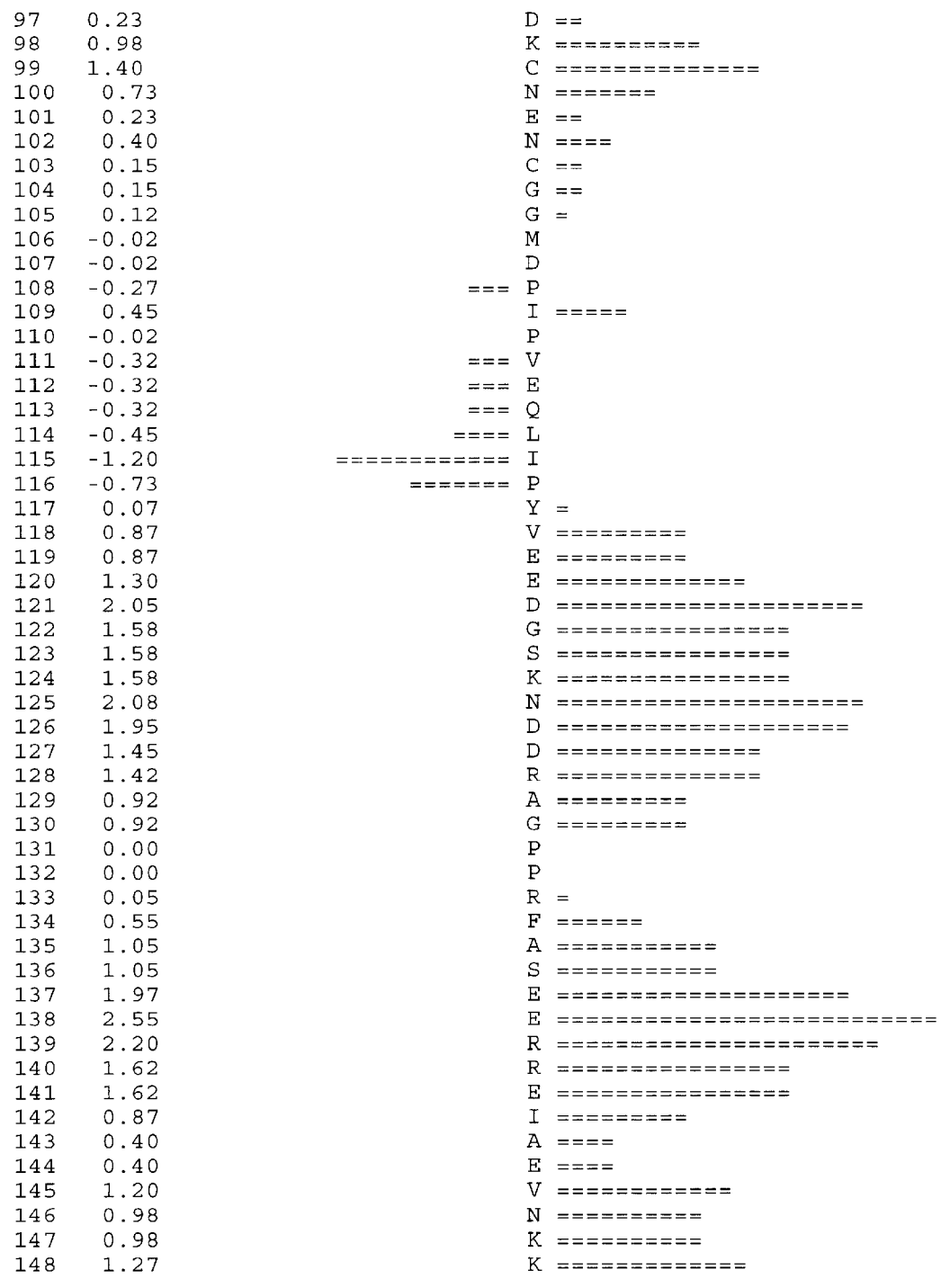

Antigenic, epitope-bearing polypeptides of the present invention are useful for raising antibodies, including monoclonal antibodies, that specifically bind to a zalpha33 protein. Antigenic, epitope-bearing polypeptides contain a sequence of at least six, often at least nine, commonly from 15 to about 30 contiguous amino acid residues of a zalpha33 protein (e.g., SEQ ID NO:2). Polypeptides comprising a larger portion of a zalpha33 protein, i.e. from 30 to 50 residues up to the entire sequence, are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions include the interdomain loops of zalpha33 and fragments thereof, particular loop C–D, which is markedly hydrophilic (see FIG. 1). Exemplary polypeptides in this regard include those comprising residues 136–141, 123–128, 119–124, 135–140, or 147–152 of SEQ ID NO:2.

Of particular interest within the present invention are polypeptides that comprise the entire four-helix bundle of a zalpha33 polypeptide (e.g., residues 41–163 of SEQ ID NO:2). Such polypeptides may further comprise all or part of one or both of the native zalpha33 amino-terminal (residues 18–40 of SEQ ID NO:2) and carboxyl-terminal (residues 164–178 of SEQ ID NO:2) regions, as well as non-zalpha33 amino acid residues or polypeptide sequences as disclosed in more detail below.

Polypeptides of the present invention can be prepared with one or more amino acid substitutions, deletions or additions as compared to SEQ ID NO:2. These changes will usually be of a minor nature, that is conservative amino acid substitutions and other changes that do not significantly affect the folding or activity of the protein or polypeptide, and include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20–25 residues, or an extension that facilitates purification (an affinity tag) as disclosed above. Two or more affinity tags may be used in combination. Polypeptides comprising affinity tags can further comprise a polypeptide linker and/or a proteolytic cleavage site between the zalpha33 polypeptide and the affinity tag. Exemplary cleavage sites include thrombin cleavage sites and factor Xa cleavage sites.

The present invention further provides a variety of other polypeptide fusions. For example, a zalpha33 polypeptide can be prepared as a fusion to a dimerizing protein as disclosed in U.S. Pat. Nos. 5,155,027 and 5,567,584. Suitable dimerizing proteins in this regard include immunoglobulin constant region domains. Immunoglobulin-zalpha33 polypeptide fusions can be expressed in genetically engineered cells to produce a variety of multimeric zalpha33 analogs. In addition, a zalpha33 polypeptide can be joined to another bioactive molecule, such as a cytokine, to provide a multi-functional molecule. One or more helices of a zalpha33 polypeptide can be joined to another cytokine to enhance or otherwise modify its biological properties. Auxiliary domains can be fused to zalpha33 polypeptides to target them to specific cells, tissues, or macromolecules (e.g., collagen). For example, a zalpha33 polypeptide or protein can be targeted to a predetermined cell type by fusing a zalpha33 polypeptide to a ligand that specifically binds to a receptor on the surface of the target cell. In this way, polypeptides and proteins can be targeted for therapeutic or diagnostic purposes. A zalpha33 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

Polypeptide fusions of the present invention will generally contain not more than about 1,500 amino acid residues, often not more than about 1,200 residues, frequently not more than about 1,000 residues, and will in many cases be considerably smaller. For example, a zalpha33 polypeptide of 161 residues (residues 18–178 of SEQ ID NO:2) can be fused to *E. coli* β-galactosidase (1,021 residues; see Casadaban et al., *J. Bacteriol.* 143:971–980, 1980), a 10-residue spacer, and a 4-residue factor Xa cleavage site to yield a polypeptide of 1,196 residues. In a second example, residues 18–178 of SEQ ID NO:2 can be fused to maltose binding protein (approximately 370 residues), a 4-residue cleavage site, and a 6-residue polyhistidine tag.

As disclosed above, the polypeptides of the present invention comprise at least 6 contiguous residues of SEQ ID NO:2 or SEQ ID NO:4. These polypeptides may further comprise additional residues as shown in SEQ ID NO:2, a variant of SEQ ID NO:2, or another protein as disclosed herein. "Variants of SEQ ID NO:2" includes polypeptides that are at least 90% or at least 95% identical to the corresponding region of SEQ ID NO:2. Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -2 | -2 | -1 | -1 | -1 | -1 | -2 | -1 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 1 | 1 | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The level of identity between amino acid sequences can be determined using the "FASTA" similarity search algorithm disclosed by Pearson and Lipman (*Proc. Natl. Acad. Sci. USA* 85:2444, 1988) and by Pearson (Meth. Enzymol. 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The present invention includes polypeptides having one or more conservative amino acid changes as compared with the amino acid sequence of SEQ ID NO:2. The BLOSUM62 matrix (Table 1) is an amino acid substitution matrix derived from about 2,000 local multiple alignments of protein sequence segments, representing highly conserved regions of more than 500 groups of related proteins (Henikoff and Henikoff, ibid.). Thus, the BLOSUM62 substitution frequencies can be used to define conservative amino acid substitutions that may be introduced into the amino acid sequences of the present invention. As used herein, the term "conservative amino acid substitution" refers to a substitution represented by a BLOSUM62 value of greater than -1. For example, an amino acid substitution is conservative if the substitution is characterized by a BLOSUM62 value of 0, 1, 2, or 3. Preferred conservative amino acid substitutions are characterized by a BLOSUM62 value of at least one 1 (e.g., 1, 2 or 3), while more preferred conservative amino acid substitutions are characterized by a BLOSUM62 value of at least 2 (e.g., 2 or 3).

The proteins of the present invention can also comprise non-naturally occuring amino acid residues. Non-naturally occuring amino acids include, without limitation, trans-3-methylproline, 2,4-methanoproline, cis-4-hydroxyproline, trans4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occuring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., Methods Enzymol. 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occuring amino acid(s) (e.g., 2-azaphenylalanine, 3-azaphenylalanine, 4-azaphenylalanine, or 4-fluorophenylalanine). The non-naturally occuring amino acid is incorporated into the protein in place of its natural counterpart. See, Koide et al., *Biochem.* 33:7470–7476, 1994. Naturally occuring amino acid residues can be converted to non-naturally occuring species by in vitro chemical modification. Chemical modification can be combined with site-directed mutagenesis to further expand the range of substitutions (Wynn and Richards, *Protein Sci.* 2:395–403, 1993).

Figure 1D:
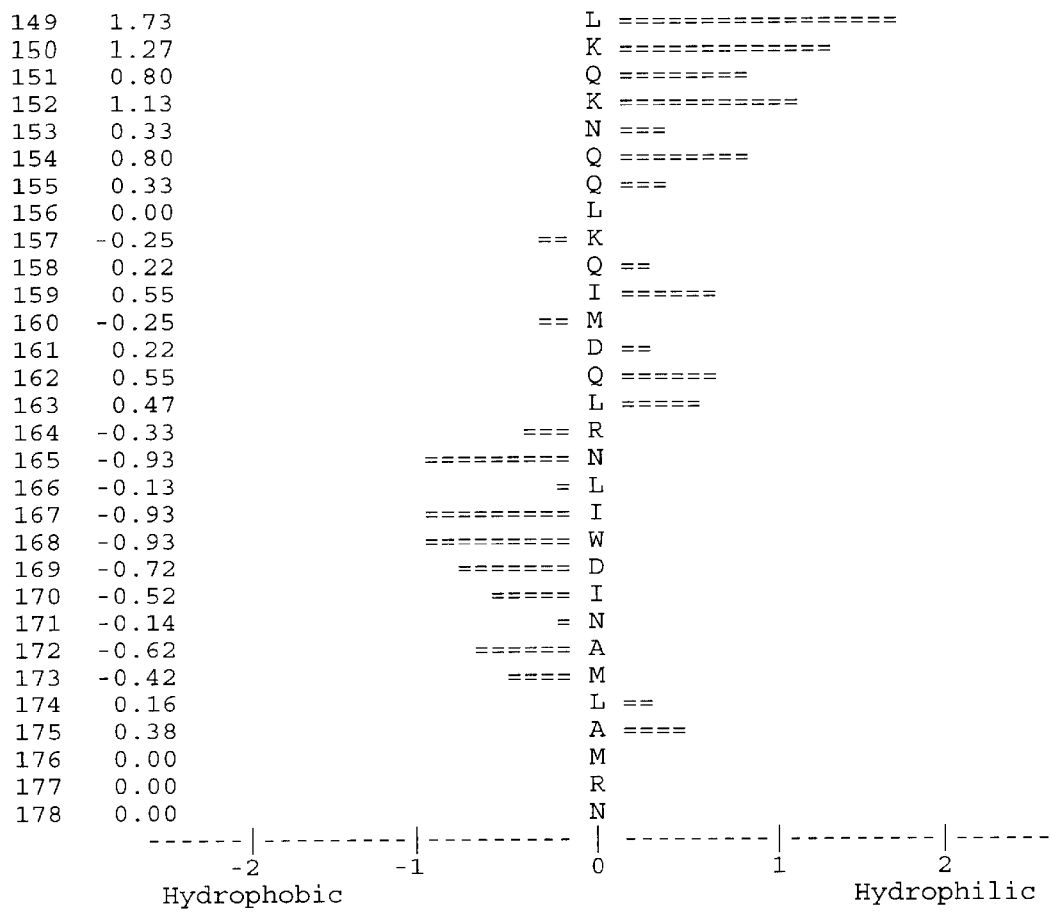

Amino acid sequence changes are made in zalpha33 polypeptides so as to minimize disruption of higher order structure essential to biological activity. For example, changes in amino acid residues will be made so as not to disrupt the four-helix bundle characteristic of the protein family. The effects of amino acid sequence changes can be predicted by computer modeling using available software (e.g., the Insight II® viewer and homology modeling tools; MSI, San Diego, Calif.) or determined by analysis of crystal structure (see, e.g., Lapthorn et al., *Nature* 369:455–461, 1994 and Lapthorn et al., *Nat. Struct. Biol.* 2:266–268, 1995). A hydrophilicity profile of SEQ ID NO:2 is shown in FIG. 1. Those skilled in the art will recognize that this hydrophilicity will be taken into account when designing alterations in the amino acid sequence of a zalpha33 polypeptide, so as not to disrupt the overall profile. Residues within the core of the four-helix bundle can be replaced with a hydrophobic residue selected from the group consisting of Leu, Ile, Val, Met, Phe, Trp, Gly, and Ala as shown in SEQ ID NO:5. Cysteine residues at positions 99 and 103 of SEQ ID NO:2 and SEQ ID NO:4 and the residues predicted to be on the exposed surface of the four-helix bundle will be relatively intolerant of substitution. Other candidate amino acid substitutions within human zalpha33 are suggested by alignment of the human (SEQ ID NO:2) and mouse (SEQ ID NO:4) sequences as shown in FIG. 2, which sequences are approximately 95% identical overall.

One skilled in the art may employ many well known techniques, independently or in combination, to analyze and compare the structural features that affect folding of a variant protein or polypeptide to a standard molecule to determine whether such modifications would be significant. One well known and accepted method for measuring folding is circular dichroism (CD). Measuring and comparing the CD spectra generated by a modified molecule and standard molecule are routine in the art (Johnson, *Proteins* 7:205–214, 1990). Crystallography is another well known and accepted method for analyzing folding and structure. Nuclear magnetic resonance (NMR), digestive peptide mapping and epitope mapping are other known methods for analyzing folding and structurally similarities between proteins and polypeptides (Schaanan et al., *Science* 257:961–964, 1992).

Essential amino acids in the polypeptides of the present invention can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity as disclosed below to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 35 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zalpha33 DNA and polypeptide sequences can be generated through DNA shuffling as disclosed by Stemmer, *Nature* 370:389–391, 1994 and Stemmer, *Proc. Natl. Acad. Sci. USA* 91:10747–10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

In many cases, the structure of the final polypeptide product will result from processing of the nascent polypeptide chain by the host cell, thus the final sequence of a zalpha33 polypeptide produced by a host cell will not always correspond to the full sequence encoded by the expressed polynucleotide. For example, expressing the complete zalpha33 sequence in a cultured mammalian cell is expected to result in removal of at least the secretory peptide, while the same polypeptide produced in a prokaryotic host would not be expected to be cleaved. Differential processing of individual chains may result in heterogeneity of expressed polypeptides.

The human and mouse zalpha33 polypeptide sequences each contain 3 cysteine residues, at positions 34, 99, and 103. Structural predictions indicate that Cys99 and Cys103 may form an intrachain disulfide bond, and that Cys34 may be free to form an interchain disulfide bond, resulting in dimerization. Actual conformation will depend in part upon the cell in which in the polypeptide is expressed. The polypeptides of the present invention thus include those comprising these cysteine residues, such as polypeptides comprising residues 34–163 or 34–178 of SEQ ID NO:2 or SEQ ID NO:4.

Zalpha33 proteins of the present invention are characterized by their activity, that is, modulation of the proliferation, differentiation, migration, adhesion, or metabolism of responsive cell types. Responsive cell types include epithelial cells and the cell lines U-373 MG (human brain glioblastoma) and 3A-Sub E (SV40-transformed human placenta). Biological activity of zalpha33 proteins is assayed using in vitro or in vivo assays designed to detect cell proliferation, differentiation, migration or adhesion; or changes in cellular metabolism (e.g., production of other growth factors or other macromolecules). Many suitable assays are known in the art, and representative assays are disclosed herein. Assays using cultured cells are most convenient for screening, such as for determining the effects of amino acid substitutions, deletions, or insertions. However, in view of the complexity of developmental processes (e.g., angiogenesis, wound healing), in vivo assays will generally be employed to confirm and further characterize biological activity. Certain in vitro models, such as the three-dimensional collagen gel matrix model of Pepper et al.

(*Biochem. Biophys. Res. Comm.* 189:824–831, 1992), are sufficiently complex to assay histological effects. Assays can be performed using exogenously produced proteins, or may be carried out in vivo or in vitro using cells expressing the polypeptide(s) of interest. Assays can be conducted using zalpha33 proteins alone or in combination with other growth factors, such as members of the VEGF family or hematopoietic cytokines (e.g., EPO, TPO, G-CSF, stem cell factor). Representative assays are disclosed below.

Mutagenesis methods as disclosed above can be combined with high volume or high-throughput screening methods to detect biological activity of zalpha33 variant polypeptides. Assays that can be scaled up for high throughput include mitogenesis assays, which can be run in a 96-well format. Mutagenized DNA molecules that encode active zalpha33 polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptide fragments or variants of SEQ ID NO:2 or SEQ ID NO:4 that retain the activity of wild-type zalpha33.

The present invention also provides polynucleotide molecules, including DNA and RNA molecules, that encode the zalpha33 polypeptides disclosed above. A representative DNA sequence encoding the amino acid sequence of SEQ ID NO:2 is shown in SEQ ID NO:1, and a representative DNA sequence encoding the amino acid sequence of SEQ ID NO:4 is shown in SEQ ID NO:3. Those skilled in the art will readily recognize that, in view of the degeneracy of the genetic code, considerable sequence variation is possible among these polynucleotide molecules. SEQ ID NO:6 is a degenerate DNA sequence that encompasses all DNAs that encode the zalpha33 polypeptide of SEQ ID NO:2. Those skilled in the art will recognize that the degenerate sequence of SEQ ID NO:6 also provides all RNA sequences encoding SEQ ID NO:2 by substituting U for T. Thus, zalpha33 polypeptide-encoding polynucleotides comprising nucleotides 1–534 or nucleotides 52–534 of SEQ ID NO:6, and their RNA equivalents are contemplated by the present invention, as are segments of SEQ ID NO:6 encoding other zalpha33 polypeptides disclosed herein. Table 2 sets forth the one-letter codes used within SEQ ID NO:6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:6, encompassing all possible codons for a given amino acid, are set forth in Table 3, below.

TABLE 3

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |
| Gap | — | — | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–912, 1980; Haas et al. *Curr. Biol.* 6:315–24, 1996; Wain-Hobson et al., *Gene* 13:355–64, 1981; Grosjean and Fiers, *Gene* 18:199–209, 1982; Holm, *Nuc. Acids Res.* 14:3075–87, 1986; and Ikemura, *J. Mol. Biol.* 158:573–97, 1982. Introduction of preferred codon sequences into recombinant DNA can, for example, enhance production of the protein by making protein translation more efficient within a particular cell type or species. Therefore, the degenerate codon sequence disclosed in SEQ ID NO:6 serves as a template for optimizing expression of polynucleotides in various cell types and species commonly used in the art and disclosed herein.

Within certain embodiments of the invention the isolated polynucleotides will hybridize to similar sized regions of SEQ ID NO:1 or SEQ ID NO:3, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of zalpha33 RNA. Suitable tissues include heart, liver, pancreas, testis, ovary, and thyroid. Zalpha33 transcripts have also been detected in B-cells and in many tumor cells. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (Proc. *Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding zalpha33 polypeptides are then identified and isolated by, for example, hybridization or PCR.

Full-length clones encoding zalpha33 can be obtained by conventional cloning procedures. Complementary DNA (cDNA) clones are often preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zalpha33, receptor fragments, or other specific binding partners.

Zalpha33 polynucleotide sequences disclosed herein can also be used as probes or primers to clone 5' non-coding regions of a zalpha33 gene. Promoter elements from a zalpha33 gene could thus be used to direct the expression of heterologous genes in, for example, transgenic animals or patients treated with gene therapy. Cloning of 5' flanking sequences also facilitates production of zalpha33 proteins by "gene activation" as disclosed in U.S. Pat. No. 5,641,670. Briefly, expression of an endogenous zalpha33 gene in a cell is altered by introducing into the zalpha33 locus a DNA construct comprising at least a targeting sequence, a regulatory sequence, an exon, and an unpaired splice donor site. The targeting sequence is a zalpha33 5' non-coding sequence that permits homologous recombination of the construct with the endogenous zalpha33 locus, whereby the sequences within the construct become operably linked with the endogenous zalpha33 coding sequence. In this way, an endogenous zalpha33 promoter can be replaced or supplemented with other regulatory sequences to provide enhanced, tissue-specific, or otherwise regulated expression.

A human zalpha33 gene sequence is shown in SEQ ID NO:10. Within SEQ ID NO:10, exons are at nucleotides 1001–1319, 8914–9072, 10,986–11,090, and 20,144–20, 597. Nucleotides 1–1000 of SEQ ID NO:2 are believed to contain promoter and regulatory elements.

Those skilled in the art will recognize that the sequences disclosed in SEQ ID NOS:1 and 2 represent a single allele of human zalpha33, and the sequences disclosed in SEQ ID NOS:3 and 4 represent a single allele of mouse zalpha33. Allelic variants of these sequences can be cloned by probing cDNA or genomic libraries from different individuals according to standard procedures.

The present invention further provides counterpart polypeptides and polynucleotides from other species ("orthologs"). Of particular interest are zalpha33 polypeptides from other mammalian species, including murine, porcine, ovine, bovine, canine, feline, equine, and other primate polypeptides. Orthologs of human zalpha33 can be cloned using information and compositions provided by the present invention in combination with conventional cloning techniques. For example, a cDNA can be cloned using mRNA obtained from a tissue or cell type that expresses zalpha33 as disclosed above. A library is then prepared from mRNA of a positive tissue or cell line. A zalpha33-encoding cDNA can then be isolated by a variety of methods, such as by probing with a complete or partial human cDNA or with one or more sets of degenerate probes based on the disclosed sequence. A cDNA can also be cloned using the polymerase chain reaction, or PCR (Mullis, U.S. Pat. No. 4,683,202), using primers designed from the representative human zalpha33 sequence disclosed herein. Within an additional method, the cDNA library can be used to transform or transfect host cells, and expression of the cDNA of interest can be detected with an antibody to zalpha33 polypeptide. Similar techniques can also be applied to the isolation of genomic clones.

For any zalpha33 polypeptide, including variants and fusion proteins, one of ordinary skill in the art can readily generate a fully degenerate polynucleotide sequence encoding that variant using the information set forth in Tables 3 and 4, above. Moreover, those of skill in the art can use standard software to devise zalpha33 variants based upon the nucleotide and amino acid sequences described herein.

The present invention thus provides a computer-readable medium encoded with a data structure that provides at least one of the following sequences: SEQ ID NO:1, SEQ ID NO:2, SEQ ID NO:3, SEQ ID NO:4, SEQ ID NO:5, SEQ ID NO:6, and portions thereof. Suitable forms of computer-readable media include magnetic media and optically-readable media. Examples of magnetic media include a hard or fixed drive, a random access memory (RAM) chip, a floppy disk, digital linear tape (DLT), a disk cache, and a ZP™ disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

The zalpha33 polypeptides of the present invention, including full-length polypeptides, biologically active fragments, and fusion polypeptides can be produced according to conventional techniques using cells into which have been introduced an expression vector encoding the polypeptide. As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, NY, 1989, and Ausubel et al., eds., *Current Protocols in Molecular Biology*, John Wiley and Sons, Inc., NY, 1987.

In general, a DNA sequence encoding a zalpha33 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zalpha33 polypeptide into the secretory pathway of a host cell, a secretory signal sequence (also known as a leader sequence, prepro sequence or pre sequence) is provided in the expression vector. The secretory signal sequence may be that of zalpha33, or may be derived from another secreted protein (e.g., t-PA; see, U.S. Pat. No. 5,641,655) or synthesized de novo. The secretory signal sequence is operably linked to the zalpha33 DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells can be used as hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1, ATCC No. CCL 61; or CHO DG44, Chasin et al., *Som. Cell. Molec. Genet.* 12:555, 1986) cell lines. Additional suitable cell lines are known in the art and available from public depositories such as the American Type Culture Collection, Manassas, Va. In general, strong transcription promoters are will be used, such as promoters from SV40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, Manassas, Va. USA under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

The adenovirus system (disclosed in more detail below) can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. In an alternative method, adenovirus vector-infected 293 cells can be grown as adherent cells or in suspension culture at relatively high cell density to produce significant amounts of protein (See Garnier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art. Within one method, recombinant baculovirus is produced through the use of a transposon-based system described by Luckow et al. (*J. Virol.* 67:4566–4579, 1993). This system, which utilizes transfer vectors, is commercially available in kit form (Bac-to-Bac™ kit; Life Technologies, Rockville, Md.). The transfer vector (e.g., pFastBacI™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a zalpha33-encoding sequence is transformed into E. coli host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zalpha33 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately 2–5×10$^5$ cells to a density of 1–2×10$^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. The use of *Agrobacterium rhizogenes* as a vector for expressing genes in plant cells has been reviewed by Sinkar et al., *J. Biosci.* (Bangalore) 11:47–58, 1987.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in Saccharomyces cerevisiae is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14,11–23, 1998. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. Production of recombinant proteins in *Pichia methanolica* is disclosed in U.S. Pat. No. 5,716,808, 5,736,383, 5,854,039, and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zalpha33 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

The polypeptides and proteins of the present invention can be purified to $\geq 80\%$ purity, to $\geq 90\%$ purity, to $\geq 95\%$ purity, or to a pharmaceutically pure state, that is greater than 99.9% pure with respect to contaminating macromolecules, particularly other proteins and nucleic acids, and free of infectious and pyrogenic agents. The desired degree of purification will depend upon the intended use of the polypeptide or protein.

Expressed recombinant zalpha33 proteins (including chimeric polypeptides and multimeric proteins) are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Biol/Technol.* 6: 1321–1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zalpha33 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

PEGylation is one method commonly used that has been demonstrated to increase plasma half-life, increase solubility, and decrease antigenicity and immunogenicity of proteins (Nucci et al., *Advanced Drug Delivery Reviews* 6:133–155, 1991 and Lu et al., *Int. J. Peptide Protein Res.* 43:127–138, 1994). Several procedures for creating and purifying pegylated proteins are known in the art. See, for example, Abuchowski et al., *J. Biol. Chem.* 252:3582–3586, 1977 and Becauchamp et al., Anal. Biochem. 131:25–33, 1983. Particular acid amino acid residues (e.g. glutamic and aspartic acids) and amino acids at the carboxyl-terminus of a protein are amenable to PEGylation (Zalipsky, *Bioconjugate Chem.* 6:150–165, 1995).

Using methods known in the art, zalpha33 proteins can be prepared as monomers or multimers; glycosylated or non-glycosylated; pegylated or non-pegylated; and may or may not include an initial methionine amino acid residue.

Target cells for use in zalpha33 activity assays include, without limitation, vascular cells (especially endothelial cells and smooth muscle cells), hematopoietic (myeloid and lymphoid) cells, liver cells (including hepatocytes, fenestrated endothelial cells, Kupffer cells, and Ito cells), fibroblasts (including human dermal fibroblasts and lung fibroblasts), fetal lung cells, articular synoviocytes, pericytes, chondrocytes, osteoblasts, and prostate epithelial cells. Endothelial cells and hematopoietic cells are derived from a common ancestral cell, the hemangioblast (Choi et al., *Development* 125:725–732, 1998).

Activity of zalpha33 proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347–354, 1990), incorporation of radiolabelled nucleotides (as disclosed by, e.g., Raines and Ross, *Methods Enzymol.* 109:749–773, 1985; Wahl et al., *Mol. Cell Biol.* 8:5016–5025, 1988; and Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., Growth Reg. 5:69–84, 1995; and Scudiero et al., *Cancer Res.* 48:4827–4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, FASEB, 5:281–284, 1991; Francis, Differentiation 57:63–75, 1994; Raes, *Adv. Anim. Cell Biol. Technol. Bioprocesses*, 161–171, 1989; all incorporated herein by reference).

Zalpha33 activity may also be detected using assays designed to measure zalpha33-induced production of one or more additional growth factors or other macromolecules. Such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), angiogenin, and other macromolecules produced by the liver. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a zalpha33 protein is measured using zymogram gels (Loita and Stetler-Stevenson, *Cancer Biology* 1:96–106, 1990). Procollagen/collagen synthesis by dermal fibroblasts and chondrocytes in response to a test protein is measured using $^3$H-proline incorporation into nascent secreted collagen. $^3$H-labeled collagen is visualized by SDS-PAGE followed by autoradiography (Unemori and Amento, *J. Biol. Chem.* 265: 10681–10685, 1990). Glycosaminoglycan (GAG) secretion from dermal fibroblasts and chondrocytes is measured using a 1,9-dimethylmethylene blue dye binding assay (Farndale et al., *Biochim. Biophys. Acta* 883:173–177, 1986). Collagen and GAG assays are also carried out in the presence of IL-1β or TGF-β to examine the ability of zalpha33 protein to modify the established responses to these cytokines.

Monocyte activation assays are carried out (1) to look for the ability of zalpha33 proteins to further stimulate monocyte activation, and (2) to examine the ability of zalpha33 proteins to modulate attachment-induced or endotoxin-induced monocyte activation (Fuhlbrigge et al., *J. Immunol.* 138: 3799–3802, 1987). IL-1α and TNFα levels produced in response to activation are measured by ELISA (Biosource, Inc. Camarillo, Calif. Monocyte/macrophage cells, by virtue of CD14 (LPS receptor), are exquisitely sensitive to endotoxin, and proteins with moderate levels of endotoxin like activity will activate these cells.

Hematopoietic activity of zalpha33 proteins can be assayed on various hematopoietic cells in culture. Suitable assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zalpha33 polypeptides on hematopoietic cell lines can be measured as disclosed above.

Cell migration is assayed essentially as disclosed by Kähler et al. (*Arteriosclerosis, Thrombosis, and Vascular Biology* 17:932–939, 1997). A protein is considered to be chemotactic if it induces migration of cells from an area of low protein concentration to an area of high protein concentration. A typical assay is performed using modified Boyden chambers with a polystryrene membrane separating the two chambers (e.g., Transwell®; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235–248; Baatout, Anticancer Research 17:451–456, 1997).

Growth factor effects of zalpha33 proteins can also be assayed in an aortic ring outgrowth assay (Nicosia and Ottinetti, *Laboratory Investigation* 63:115, 1990; Villaschi and Nicosia, *Am. J. Pathology* 143:181–190, 1993).

Cell adhesion activity is assayed essentially as disclosed by LaFleur et al. (*J. Biol. Chem.* 272:32798–32803, 1997). Briefly, microtiter plates are coated with the test protein, non-specific sites are blocked with BSA, and cells (such as smooth muscle cells, leukocytes, or endothelial cells) are plated at a density of approximately $10^4$–$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

The activity of zalpha33 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906–1912, 1992; Pitchford et al., *Meth. Enzymol.* 228:84–108, 1997; Arimilli et al., *J. Immunol. Meth.* 212:49–59, 1998; and Van Liefde et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zalpha33 proteins, their agonists, and antagonists. The microphysiometer can be used to measure responses of a zalpha33-responsive eukaryotic cell, compared to a control eukaryotic cell that does not respond to zalpha33 polypeptide. Zalpha33-responsive eukaryotic cells comprise cells into which a receptor for zalpha33 has been transfected creating a cell that is responsive to zalpha33, as well as cells naturally responsive to zalpha33 such as cells derived from vascular tissue. Differences, measured by a change in extracellular acidification, in the response of cells exposed to zalpha33 polypeptide relative to a control not exposed to zalpha33, are a direct measurement of zalpha33-modulated cellular responses. Moreover, such zalpha33-modulated responses can be assayed under a variety of stimuli. The present invention thus provides methods of identifying agonists and antagonists of zalpha33 proteins, comprising providing cells responsive to a zalpha33 polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Culturing a third portion of the cells in the presence of a zalpha33 protein and the absence of a test compound provides a positive control for the zalpha33-responsive cells and a control to compare the agonist activity of a test compound with that of the zalpha33 polypeptide. Antagonists of, zalpha33 can be identified by exposing the cells to zalpha33 protein in the presence and absence of the test compound, whereby a reduction in zalpha33-stimulated activity is indicative of antagonist activity in the test compound.

Expression of zalpha33 polynucleotides in animals provides models for further study of the biological effects of overproduction or inhibition of protein activity in vivo. Zalpha33-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

Transgenic mice, engineered to express a zalpha33 gene, and mice that exhibit a complete absence of zalpha33 gene function, referred to as "knockout mice" (Snouwaert et al., *Science* 257:1083, 1992), can also be generated (Lowell et al., *Nature* 366:740–742, 1993). These mice can be employed to study the zalpha33 gene and the protein encoded thereby in an in vivo system. Transgenic mice are particularly useful for investigating the role of zalpha33 proteins in early development in that they allow the identification of developmental abnormalities or blocks resulting from the over- or underexpression of a specific factor. See also, Maisonpierre et al., *Science* 277:55–60, 1997 and Hanahan, *Science* 277:48–50, 1997. Suitable promoters for transgenic expression include promoters from metallothionein and albumin genes.

Antisense methodology can be used to inhibit zalpha33 gene transcription to examine the effects of such inhibition in vivo. Polynucleotides that are complementary to a segment of a zalpha33-encoding polynucleotide (e.g., a polynucleotide as set forth in SEQ ID NO:1) are designed to bind to zalpha33-encoding mRNA and to inhibit translation of such mRNA. Such antisense oligonucleotides can also be used to inhibit expression of zalpha33 polypeptide-encoding genes in cell culture.

Most four-helix bundle cytokines as well as other proteins produced by activated lymphocytes play an important biological role in cell differentiation, activation, recruitment and homeostasis of cells throughout the body. Zalpha33 and inhibitors of zalpha33 activity are expected to have a variety of therapeutic applications. These therapeutic applications include treatment of diseases which require immune regulation, including autoimmune diseases such as rheumatoid arthritis, multiple sclerosis, myasthenia gravis, systemic lupus erythematosis, and diabetes. Zalpha33 may be important in the regulation of inflammation, and therefore would be useful in treating rheumatoid arthritis, asthma and sepsis. There may be a role of zalpha33 in mediating tumorigenesis, whereby a zalpha33 antagonist would be useful in the treatment of cancer. Zalpha33 may be useful in modulating the immune system, whereby zalpha33 and zalpha33 antagonists may be used for reducing graft rejection, preventing graft-vs-host disease, boosting immunity to infectious diseases, treating immunocompromised patients (e.g., HIV$^+$ patients), or in improving vaccines.

Zalpha33 polypeptides can be administered alone or in combination with other vasculogenic or angiogenic agents, including VEGF. When using zalpha33 in combination with an additional agent, the two compounds can be administered simultaneously or sequentially as appropriate for the specific condition being treated.

For pharmaceutical use, zalpha33 proteins are formulated for topical or parenteral, particularly intravenous or subcutaneous, delivery according to conventional methods. In general, pharmaceutical formulations will include a zalpha33 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa, 19th ed., 1995. Zalpha33 will usually be used in a concentration of about 10 to 100 μg/ml of total volume, although concentrations in the range of 1 ng/ml to 1000 μg/ml may be used. For topical application, such as for the promotion of wound healing, the protein will be applied in the range of 0.1–10 μg/cm$^2$ of wound area, with the exact dose determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a therapeutically effective amount of zalpha33 is an amount sufficient to produce a clinically significant change in the treated condition, such as a clinically significant change in hematopoietic or immune function, a significant reduction in morbidity, or a significantly increased histological score.

Zalpha33 proteins, agonists, and antagonists are useful for modulating the expansion, proliferation, activation, differentiation, migration, or metabolism of responsive cell types, which include both primary cells and cultured cell lines. Of particular interest in this regard are hematopoietic cells (including stem cells and mature myeloid and lymphoid cells), endothelial cells, smooth muscle cells, fibroblasts, and hepatocytes. Zalpha33 polypeptides are added to tissue culture media for these cell types at a concentration of about 10 pg/ml to about 100 ng/ml. Those skilled in the art will recognize that zalpha33 proteins can be advantageously combined with other growth factors in culture media.

Within the laboratory research field, zalpha33 proteins can also be used as molecular weight standards or as reagents in assays for determining circulating levels of the protein, such as in the diagnosis of disorders characterized by over- or under-production of zalpha33 protein or in the analysis of cell phenotype.

Zalpha33 proteins can also be used to identify inhibitors of their activity. Test compounds are added to the assays disclosed above to identify compounds that inhibit the activity of zalpha33 protein. In addition to those assays disclosed above, samples can be tested for inhibition of zalpha33 activity within a variety of assays designed to measure receptor binding or the stimulation/inhibition of zalpha33-dependent cellular responses. For example, zalpha33-responsive cell lines can be transfected with a reporter gene construct that is responsive to a zalpha33-stimulated cellular pathway. Reporter gene constructs of this type are known in the art, and will generally comprise a zalpha33-activated serum response element (SRE) operably linked to a gene encoding an assayable protein, such as luciferase. Candidate compounds, solutions, mixtures or extracts are tested for the ability to inhibit the activity of zalpha33 on the target cells as evidenced by a decrease in zalpha33 stimulation of reporter gene expression. Assays of this type will detect compounds that directly block zalpha33 binding to cell-surface receptors, as well as compounds that block processes in the cellular pathway subsequent to receptor-ligand binding. In the alternative, compounds or other samples can be tested for direct blocking of zalpha33 binding to receptor using zalpha33 tagged with a detectable label (e.g., $^{125}$I, biotin, horseradish peroxidase, FITC, and the like). Within assays of this type, the ability of a test sample to inhibit the binding of labeled zalpha33 to the receptor is indicative of inhibitory activity, which can be confirmed through secondary assays. Receptors used within binding assays may be cellular receptors or isolated, immobilized receptors.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to a zalpha33 polypeptide or protein with an affinity at least 10-fold greater than the binding affinity to control (non-zalpha33) polypeptide or protein. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, FL, 1982, which is incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of a zalpha33 polypeptide may be increased through the use of an adjuvant such as alum (aluminum hydroxide) or Freund's complete or incomplete adjuvant. Polypeptides useful for immunization also include fusion polypeptides, such as fusions of a zalpha33 polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immnunization.

Alternative techniques for generating or selecting antibodies include in vitro exposure of lymphocytes to zalpha33 polypeptides, and selection of antibody display libraries in phage or similar vectors (e.g., through the use of immobilized or labeled zalpha33 polypeptide). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

A variety of assays known to those skilled in the art can be utilized to detect antibodies which specifically bind to zalpha33 polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zalpha33 may be used for affinity purification of the protein, within diagnostic assays for determining circulating levels of the protein; for detecting or quantitating soluble zalpha33 polypeptide as a marker of underlying pathology or disease; for immunolocalization within whole animals or tissue sections, including immunodiagnostic applications; for immunohistochemistry; and as antagonists to block protein activity in vitro and in vivo. Antibodies to zalpha33 may also be used for tagging cells that express zalpha33; for affinity purification of zalpha33 polypeptides and proteins; in analytical methods employing FACS; for screening expression libraries; and for generating anti-idiotypic antibodies. Antibodies can be linked to other compounds, including therapeutic and diagnostic agents, using known methods to provide for targetting of those compounds to cells expressing receptors for zalpha33. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention may also be directly or indirectly conjugated to drugs, toxins, radionuclides and the like, and these conjugates used for in vivo diagnostic or therapeutic applications(e.g., inhibition of cell proliferation). See, in general, Ramakrishnan et al., *Cancer Res.* 56:1324–1330, 1996.

Polypeptides and proteins of the present invention can be used to identify and isolate receptors. Zalpha33 receptors may be involved in growth regulation in the liver, blood vessel formation, and other developmental processes. For example, zalpha33 proteins and polypeptides can be immobilized on a column, and membrane preparations run over the column (as generally disclosed in *Immobilized Affinity Ligand Techniques*, Hermanson et al., eds., Academic Press, San Diego, Calif., 1992, pp.195–202). Proteins and polypeptides can also be radiolabeled (*Methods Enzymol.*, vol. 182, "Guide to Protein Purification", M. Deutscher, ed., Academic Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and used to tag specific cell-surface proteins. In a similar manner, radiolabeled zalpha33 proteins and polypeptides can be used to clone the cognate receptor in binding assays using cells transfected with an expression cDNA library.

The present invention also provides reagents for use in diagnostic applications. For example, the zalpha33 gene, a probe comprising zalpha33 DNA or RNA, or a subsequence thereof can be used to determine the presence of mutations at or near the zalpha33 locus. Detectable chromosomal aberrations at the zalpha33 gene locus include, but are not limited to, aneuploidy, gene copy number changes, insertions, deletions, restriction site changes, and rearrangements. These aberrations can occur within the coding sequence, within introns, or within flanking sequences, including upstream promoter and regulatory regions, and may be manifested as physical alterations within a coding sequence or changes in gene expression level. Analytical probes will generally be at least 20 nucleotides in length, although somewhat shorter probes (14–17 nucleotides) can be used. PCR primers are at least 5 nucleotides in length, often 15 or more nt, commonly 20–30 nt. Short polynucleotides can be used when a small region of the gene is targetted for analysis. For gross analysis of genes, a polynucleotide probe may comprise an entire exon or more. Probes will generally comprise a polynucleotide linked to a signal-generating moiety such as a radionucleotide. In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (c) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof.

Suitable assay methods in this regard include molecular genetic techniques known to those in the art, such as restriction fragment length polymorphism (RFLP) analysis, 10 short tandem repeat (STR) analysis employing PCR techniques, ligation chain reaction (Barany, PCR *Methods and Applications* 1:5–16, 1991), ribonuclease protection assays, and other genetic linkage analysis techniques known in the art (Sambrook et al., ibid.; Ausubel et. al., ibid.; A. J. Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, PCR *Methods and Applications* 1:34–38, 1999).

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels that cover the entire human genome are commercially available, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest, and the establishment of directly proportional physical distances between newly discovered genes of interest and previously mapped markers. The precise knowledge of a gene's position can be useful for a number of purposes, including:1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank (National Center for Biological Information, National Institutes of Health, Bethesda, Md. http://www.ncbi.nlm.nih.gov), and can be searched with a gene sequence of interest for the mapping data contained within these short genomic landmark STS sequences.

The polypeptides, nucleic acid and/or antibodies of the present invention may be used in diagnosis or treatment of disorders associated with cell loss or abnormal cell proliferation (including cancer). Labeled zalpha33 polypeptides may be used for imaging tumors or other sites of abnormal cell proliferation.

Inhibitors of zalpha33 activity (zalpha33 antagonists) include anti-zalpha33 antibodies and soluble zalpha33 receptors, as well as other peptidic and non-peptidic agents (including ribozymes). Such antagonists can be used to block the effects of zalpha33 on cells or tissues. Of particular interest is the use of antagonists of zalpha33 activity in cancer therapy. As early detection methods improve it becomes possible to intervene at earlier times in tumor development, making it feasible to use inhibitors of growth factors to block cell proliferation, angiogenesis, and other events that lead to tumor development and metastasis. Inhibitors are also expected to be useful in adjunct therapy after surgery to prevent the growth of residual cancer cells. Inhibitors can also be used in combination with other cancer therapeutic agents.

In addition to antibodies, zalpha33 inhibitors include small molecule inhibitors and inactive receptor-binding fragments of zalpha33 polypeptides. Inhibitors are formulated for pharmaceutical use as generally disclosed above, taking into account the precise chemical and physical nature of the inhibitor and the condition to be treated. The relevant determinations are within the level of ordinary skill in the formulation art.

Polynucleotides encoding zalpha33 polypeptides are useful within gene therapy applications where it is desired to increase or inhibit zalpha33 activity. If a mammal has a mutated or absent zalpha33 gene, a zalpha33 gene can be introduced into the cells of the mammal. In one embodiment, a gene encoding a zalpha33 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are commonly used. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSVI) vector (Kaplitt et al., *Molec. Cell. Neurosci.* 2:320–330, 1991); an attenuated adenovirus vector, such as the vector described by Stratford-Perricaudet et al., *J. Clin. Invest.* 90:626–630, 1992; and a defective adeno-associated virus vector (Samulski et al., *J. Virol.* 61:3096–3101, 1987; Samulski et al., *J. Virol.* 63:3822–3888, 1989). Within another embodiment, a zalpha33 gene can be introduced in a retroviral vector as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 15 62:1120, 1988; Temin et al., U.S. Pat. No. 5,124,263; Dougherty et al., WIPO Publication WO 95/07358; and Kuo et al., *Blood* 82:845, 1993. Alternatively, the vector can be introduced by liposome-mediated transfection ("lipofection"). Synthetic cationic lipids can be used to prepare liposomes for in vivo transfection of a gene encoding a marker (Felgner et al., *Proc. Natl. Acad. Sci. USA* 84:7413–7417, 1987; Mackey et al., *Proc. Natl. Acad. Sci. USA* 85:8027–8031, 1988). The use of lipofection to introduce exogenous genes into specific organs in vivo has certain practical advantages, including molecular targeting of liposomes to specific cells. Directing transfection to particular cell types is particularly advantageous in a tissue with cellular heterogeneity, such as the pancreas, liver, kidney, and brain. Lipids may be chemically coupled to other molecules for the purpose of targeting. Peptidic and non-peptidic molecules can be coupled to liposomes chemically. Within another embodiment, cells are removed from the body, a vector is introduced into the cells as a naked DNA plasmid, and the transformed cells are re-implanted into the body as disclosed above.

Antisense methodology can be used to inhibit zalpha33 gene transcription in a patient as generally disclosed above.

Zalpha33 polypeptides and anti-zalpha33 antibodies can be directly or indirectly conjugated to drugs, toxins, radio-nuclides and the like, and these conjugates used for in vivo diagnostic or therapeutic applications. For instance, polypeptides or antibodies of the present invention may be used to identify or treat tissues or organs that express a corresponding anti-complementary molecule (receptor or antigen, respectively, for instance). More specifically, zalpha33 polypeptides or anti-zalpha33 antibodies, or bioactive fragments or portions thereof, can be coupled to detectable or cytotoxic molecules and delivered to a mammal having cells, tissues, or organs that express the anti-complementary molecule.

Suitable detectable molecules can be directly or indirectly attached to the polypeptide or antibody, and include radionuclides, enzymes, substrates, cofactors, inhibitors, fluorescent markers, chemiluminescent markers, magnetic particles, and the like. Suitable cytotoxic molecules can be directly or indirectly attached to the polypeptide or antibody, and include bacterial or plant toxins (for instance, diphtheria toxin, Pseudomonas exotoxin, ricin, abrin, saporin, and the like), as well as therapeutic radionuclides, such as iodine-131, rhenium-188 or yttrium-90. These can be either directly attached to the polypeptide or antibody, or indirectly attached according to known methods, such as through a chelating moiety. Polypeptides or antibodies can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

Polypeptide-toxin fusion proteins or antibody/fragment-toxin fusion proteins may be used for targeted cell or tissue inhibition or ablation, such as in cancer therapy. Of particular interest in this regard are conjugates of a zalpha33 polypeptide and a cytotoxin, which can be used to target the cytotoxin to a tumor or other tissue that is undergoing undesired angiogenesis or neovascularization. Target cells (i.e., those displaying the zalpha33 receptor) bind the zalpha33-toxin conjugate, which is then internalized, killing the cell. The effects of receptor-specific cell killing (target ablation) are revealed by changes in whole animal physiology or through histological examination. Thus, ligand-dependent, receptor-directed cyotoxicity can be used to enhance understanding of the physiological significance of a protein ligand. An exemplary toxin is saporin. Mammalian cells have no receptor for saporin, which is non-toxic when it remains extracellular.

In another embodiment, zalpha33-cytokine fusion proteins or antibody/fragment-cytokine fusion proteins may be used for enhancing in vitro cytotoxicity (for instance, that mediated by monoclonal antibodies against tumor targets) and for enhancing in vivo killing of target tissues (for example, blood and bone marrow cancers). See, generally, Hornick et al., *Blood* 89:4437–4447, 1997). In general, cytokines are toxic if administered systemically. The described fusion proteins enable targeting of a cytokine to a desired site of action, such as a cell having binding sites for zalpha33, thereby providing an elevated local concentration of cytokine. Suitable cytokines for this purpose include, for example, interleukin-2 and granulocyte-macrophage colony-stimulating factor (GM-CSF). Such fusion proteins may be used to cause cytokine-induced killing of tumors and other tissues undergoing angiogenesis or neovascularization.

The bioactive polypeptide or antibody conjugates described herein can be delivered intravenously, intra-arterially or intraductally, or may be introduced locally at the intended site of action.

The invention is further illustrated by the following non-limiting examples.

EXAMPLE 1

Analysis of tissue distribution was performed by the Northern blotting technique using commercially available Blots of human RNA (Human Multiple Tissue Northern Blots I, II, and III; and Master Dot Blots; Clontech Laboratories, Inc., Palo Alto, Calif.). A probe was obtained by restriction digest of a human zalpha33 clone with EcoRI and PvuII, resulting in two cDNA fragments of 288 bp and 326 bp. The reaction mixture was electrophoresed on a 2% agarose gel, and the corresponding bands were excised and purified using commercially available gel purification reagents and protocol (QIAEX® II gel extraction kit; Qiagen, Valencia, Calif.). The purified DNA was radioactively labeled with $^{32}P$ using a commercially available kit (Rediprime™ II20 random-prime labeling system; Amersham C was purified using a commmercially available size exclusion column (NucTrap® column; Stratagene, La Jolla, Calif.). A commercially available hybridization solution (ExpressHyb™ Hybridization Solution; Clontech Laboratories Inc., Palo Alto, Calif.) was used for hybridization and prehybridization. The final hybridization solution contained 8 ml ExpressHyb™ solution, 80 µl sheared salmon sperm DNA (10 mg/ml; obtained from 5 Prime-3 Prime, Boulder, Colo.) and $1.6 \times 10^7$ cpm labeled probe. Hybridization took place overnight at 55° C. After hybridization the blots were washed in 2×SSC, 0.1% SDS at room temperature; then in 2×SSC, 0.1% SDS at 60° C. followed by a 0.1×SSC, 0.1% SDS wash at 60° C. The blots were exposed to film (Biomax AR film, Eastman Kodak Co., Rochester N.Y.) for three days and developed.

One major transcript size was observed on the Human Multiple Tissue blots at ~1.0 kb in all tissues. The signal was strongest in heart, liver, pancreas, testis, ovary, and thyroid tissue, with other tissues showing moderately lower expression levels. Signals on the Master Dot blot were present in all tisues with slightly higher signals in aorta, testis, pituitary gland, thyroid gland, mamary gland, thymus, lung, fetal thymus, and fetal lung. Expression was also seen in blots of THP1 and U937 monocyte cell lines.

EXAMPLE 2

An expression plasmid encoding full-length mouse zalpha33 was constructed using the expression vector pEZE2. The vector pEZE2 was derived from pDC312 by the addition of additional restriction enzyme recognition sites to the multiple cloning site. pDC312 and pEZE2 contain an EASE segment, as described in WO 97/25420, which can improve expression of recombinant proteins two- to eight-fold in mammalian cells (e.g., Chinese Hamster Ovary (CHO) cells). The pEZE2 expression unit contains the CMV enhancer/promoter, the adenovirus tripartite leader sequence, a multiple cloning site for insertion of the coding region for the recombinant protein, an encephalomyocarditis virus internal ribosome entry site, a coding segment for mouse dihydrofolate reductase, and the SV40 transcription terminator. In addition, pEZE2 contains an E. coli origin of replication and a bacterial beta-lactamase gene.

A DNA fragment encoding zalpha33 with a C-terminal Glu-Glu tag (zalpha33CEE) was generated by PCR using a commercially available kit (Advantage® 2 PCR Kit, Clontech, Palo Alto, Calif.). The fragment included 5' FseI and 3' AscI sites for direct cloning into the expression vector. The 5' primer contained an FseI site, a Kozak sequence, and the first 31 base pairs of the native leader sequence for zalpha33. The 3' primer contained the last 18 base pairs of zalpha33, a Glu-Glu tag sequence, a stop codon, and an AscI site. The PCR mixture included 1ul of template (plasmid containing the full-length mouse zalpha33 sequence). The reaction was run at 94° C., 1 minute; then 25 cycles of 94° C., 30 seconds; 55° C., 30 seconds; 68° C., 1 minute; then a final extension at 72° C. for 7 minutes. The PCR-generated fragment was purified using a commercially available kit (Qiaquick™ PCR Purification Kit, Qiagen Inc., Valencia, Calif.) and digested with restriction enzymes AscI and FseI (New England Biolabs, Beverly, Mass.) in a single, 100-µl reaction. Five micrograms of the expression vector pEZE2 were also digested with FseI and AscI in a single, 100-µl reaction. The digested DNA was fractionated by agarose gel electrophoresis, and the DNA fragments were isolated and purified using a commercially available kit (Qiaquick™ Gel Extraction Kit, Qiagen Inc.).

Five microliters of the zalpha33CEE DNA fragment and 1 µl of the pEZE2 vector fragment were ligated overnight at room temperature using T4 DNA ligase (high concentration) and reaction buffer obtained from New England Biolabs, Beverly, Mass. One microliter of the ligation mixture was added to 25 µl of electrocompetent E. coli strain DH1OB (Life Technologies) in a 0.2-cm cuvette. The mixture was electroporated (BioRad E. coli Pulser) at 2.3 kv. To the cuvette, 1 mL of LB broth was added, and 100 µl of the mix was plated onto LB/Ampicillin agar plates. The plates were incubated overnight at 37° C., and 16 isolated colonies were picked for DNA mini prep using a commercially available kit (obtained from Qiagen Inc.).

Individual clones were screened by PCR for the presence of zalpha33CEE DNA, using the above-mentioned primers. DNA sequencing was performed on clones #1–6, to verify the correct full-length sequence. One clone contained the correct expected sequence, from which DNA was prepared using a commercially available kit (Qiagen ® Plasmid Maxi Kit, Qiagen Inc.). The plasmid was designated pKFO248.

EXAMPLE 3

Plasmid pKFO248 was prepared for transfection into Chinese hamster ovary (CHO) cells. To insure sterility a single ethanol precipitation step was performed by combining 200 µg of plasmid DNA with 20 µl of 10mg/ml sheared salmon sperm carrier DNA (5'→3' Inc. Boulder, Colo.), 22 µl of 3M sodium acetate (pH 5.2), and 484 µl of 100% ethanol (Gold Shield Chemical Co., Hayward, Calif.) and incubating the mixture on ice for 25 minutes. After incubation, the mixture was spun at 14,000 RPM in a microcentrifuge at 4° C., the supernatant was removed, and the pellet was washed twice with 0.5 ml 70% ethanol and allowed to air dry until it appeared as an opaque white color.

Protein-free and serum-free suspension-adapted CHO DG44 cells (Chasin et al., Som. Cell. Molec. Genet. 12:555–666, 1986) were taken from a frozen stock (passage 36) and preparerd for transfection by culturing in PFCHO media (JRH Biosciences, Lenexa, Kas.), 4 mM L-Glutamine, (JRH Biosciences), and 1×HT Supplement (Life Technologies Lot #1024782) at 37° C. and 5% $CO_2$ in shake flasks at 120 RPM on a rotating shaker platform. The cells were allowed to recover from the process of thaw before being transfected at passage 38 with the plasmid zalpha 33 Mouse-CEE/pEZE2 (PKFO 248 linearized with Fsp) by High Copy Electroporation.

The CHO DG44 cells were transfected by electroporation. While the DNA pellet was drying, 10e6 total cells (16.5ml) were spun in a 25 ml conical centrifuge tube at 900 RPM for 5 minutes. The cells were resuspended into a total volume of 300 µl in PFCHO media as above and placed in an electroporation cuvette with a 0.4 cm electrode gap (Gene Pulser ® Cuvette; Bio-Rad Laboratories, Inc., Hercules, Calif.). After approximately 50 minutes of drying time the plasmid DNA was resuspended into 500 µl of PFCHO growth media and added to the cuvette so that the total volume did not exceed 800 microliters. The mixture was allowed to sit at room temperature for 5 minutes to decrease bubble formation. The cuvette was placed in an electroporator (Gene Pulser® II; Bio-Rad Laboratories, Inc.) set at 0.296 kV and 0.950 HC (high capacitance) and electroporated immediately with an actual reading of 0.310 kV and a time constant of 15.7 milliseconds.

The cells were allowed to sit 5 minutes at room temperature to recover before placement in 20 ml total volume of PFCHO media in a tissue culture flask using a sterile glass 9-inch transfer pipet previously baked for 4 hours at 260° C. The flask was placed at 37° C. and 5% $CO_2$ for 48 hours, at which time the cells were counted by hemocytometer utilizing trypan blue exclusion and put into PFCHO selection media without HT supplement and containing 200 mM methotrexate (Cal Biochem; San Diego, Calif.).

Upon recovery from the selection process conditioned media containing the secreted zalpha 33 protein is assayed by Western Blot. Neat 72-hour conditioned media is diluted 1:2 in reducing sample buffer (NuPAGE™ 2× buffer; Novex, San Diego, Calif. ) containing 100 mM DTT (ICN Biochemicals, Costa Mesa, Calif.), and 25-μl samples are loaded into appropriate wells of a 1.0 mM×12 well, 4–12% Bis-Tris Gel (NuPAGE™; Novex) and run at 150 volts for approximateley one hour. The gel is run with a protein standard (Glu-Glu tagged leptin produced in *Pichia methanolica*) is serially diluted ranging from 100 ng down to 6.25 ng total per lane and 10 μl of commercially available molecular weight markers (SeeBlue™; Novex). Proteins are transferred to a 0.2 μm nitrocellulose membrane (Novex) at 30 volts for approximately one hour. The blot is blocked in 10% nonfat dry milk (Carnation) in Western A buffer (0.25% gelatin, 50mM Tris-HCl pH 7.4, 150 mM NaCl, 5mM EDTA, 0.05% octylphenylpolyethylene glycol (Igepal ®-CA630)) either overnight at 4° C. or for one hour at room temperature on a rotating shaker platform. Thirty ml of mouse anti-Glu-Glu monoclonal antibody (BabCO Berkeley Antibody Company, Richmond, Calif.) diluted to 0.1 μg/ml in 2.5% nonfat dry milk in Western A is overlayed on the membrane, and the blot is incubated at room temperature on a rotating platform for one hour. The antibody solution is then discarded, and the membrane is rinsed three times (about 50 ml each time) with Western A. The blot is then incubated with 30 ml of goat anti-mouse IgG-HRP secondary antibody (1 mg/ml; Santa Cruz Biotechnology, Inc., Santa Cruz, Calif.) at a 1:2000 dilution under the same conditions for one hour. The secondary antibody solution is discarded and the membrane rinsed as described above. protein is detected by chemiluminescence using commercially available reagents (ECL™ Plus Western Blotting Detection System; Amersham Pharmacia Biotech, Inc., Piscataway, N.J.) and inctrumentation (Lumi-Imager™ F1; Roche Molecular Biochemicals, Indianapolis, Ind.).

EXAMPLE 4

The protein coding region of mouse zalpha33 was amplified by PCR using primers that added FseI and AscI restriction sites at the 5' and 3' termini respectively. PCR primers ZC23310 (SEQ ID NO:8) and ZC23311 (SEQ ID NO:9) were used with template plasmid containing the full-length mouse zalpha33 cDNA in a PCR reaction as follows: one cycle at 95° C. for 5 minutes; followed by 15 cycles at 95° C. for 0.5 min., 58° C. for 0.5 min., and 72° C. for 0.5 min.; followed by 72° C. for 10 min.; followed by a 4° C. soak. The PCR reaction product was loaded onto a 1.2% (low melt) agarose (SeaPlaque ® GTG; FMC Corp, Rockland, Me.) gel in TAE buffer (0.04 M Tris-acetate, 0.001 M EDTA). The zalpha33 PCR product was excised from the gel. The gel slice was melted at 65° C., extracted twice with an equal volume of Tris-buffered phenol, and EtOH precipitated. The DNA was resuspended in 10 μl dH₂O, digested with FseI-AscI, phenol/chloroform extracted, EtOH precipitated, and rehydrated in 20 μl TE (Tris/EDTA pH 8). The 537-bp zalpha33 fragment was then ligated into the FseI-AscI sites of a modified pAdTrack CMV (He et al., *Proc. Natl. Acad. Sci. USA* 95:2509–2514, 1998). This construct also contained the green fluorescent protein (GFP) marker gene. The CMV promoter driving GFP expression was replaced with the SV40 promoter, and the SV40 polyadenylation signal was replaced with the human growth hormone polyadenylation signal. In addition, the native polylinker was replaced with FseI, EcoRV, and AscI sites. This modified form of pAdTrack CMV was named pZyTrack. Ligation was performed using a DNA ligation and screening kit (Fast-Link™; Epicentre Technologies, Madison, Wis.). Clones containing the zalpha33 cDNA were identified by standard miniprep procedures. To linearize the plasmid, approximately 5 μg of the pZyTrack zalpha33 plasmid was digested with PmeI. Approximately 1 μg of the linearized plasmid was cotransformed with 200 ng of supercoiled pAdEasy (He et al., ibid.) into BJ5183 cells using an electroporator (Gene Pulser®; Bio-Rad Laboratories, Inc.) set at 2.5kV, 200 ohms, and 25μFa. The entire co-transformation was plated on 4 LB plates containing 25 μg/ml kanamycin. The smallest colonies were picked and expanded in LB/kanamycin, and recombinant adenovirus DNA was identified by standard DNA miniprep procedures. Digestion of the recombinant adenovirus DNA with FseI-AscI confirmed the presence of the zalpha33 sequence. The recombinant adenovirus miniprep DNA was transformed into *E. coli* strain DH10B™ (Life Technologies, Gaithersburg, Md.) competent cells, and DNA was prepared by anion exchange chromatography using a commercially available plasmid isolation kit (QIAGEN ® Plasmid Maxi Kit; Qiagen, Inc., Valencia, Calif.).

Approximately 5 μg of recombinant adenoviral DNA was digested with PacI enzyme (New England Biolabs) for 3 hours at 37° C. in a reaction volume of 100 μl containing 20–30U of PacI. The digested DNA was extracted twice with an equal volume of phenol/chloroform and precipitated with ethanol. The DNA pellet was resuspended in 5 μl distilled water. A T25 flask of QBI-293A cells (Quantum Biotechnologies, Inc., Montreal, Canada), inoculated the day before and grown to 60–70% confluence, was transfected with the PacI-digested DNA. The PacI-digested DNA was diluted up to a total volume of 50 μl with sterile HBS (150 mM NaCl, 20 mM HEPES). In a separate tube, 25 μl of 1 mg/ml N-[1-(2,3-Dioleoyloxy)propyl]-N,N,N-trimethyl-ammonium salts (DOTAP) (Boehringer Mannheim, Indianapolis, Ind.) was diluted to a total volume of 100 μl with HBS. The DNA was added to the DOTAP, mixed gently by pipeting up and down, and left at room temperature for 15 minutes. The media was removed from the 293A cells, and the cells were washed with 5 ml serum-free MEMalpha containing 1 mM sodium pyruvate, 0.1 mM MEM non-essential amino acids, and 25 mM HEPES buffer (media components obtained from Life Technologies, Gaithersburg, Md.). 5 ml of serum-free MEM was added to the 293A cells and held at 37° C. The DNA/lipid mixture was added drop-wise to the T25 flask of 293A cells, mixed gently, and incubated at 37° C. for 4 hours. After 4 hours the media containing the DNA/lipid mixture was aspirated off and replaced with 5 ml complete MEM containing 5% fetal bovine serum. The transfected cells were monitored for GFP expression and formation of foci (viral plaques).

Seven days after transfection of 293A cells with the recombinant adenoviral DNA, the cells expressed the GFP protein and started to form foci. The crude viral lysate was collected with a cell scraper and transferred to a 50-ml conical tube. To release most of the virus particles from the cells, three freeze/thaw cycles were done in a dry ice/ethanol bath and a 37° waterbath.

The crude lysate was amplified (primary (1°) amplification) to obtain a working "stock" of zalpha33 recombinant adenovirus (rAdV) lysate. Ten 10-cm plates of nearly confluent (80–90%) 293A cells were set up 20 hours in advance. 200 ml of crude rAdV lysate was added to each 10-cm plate, and the plates were monitored for 48 to 72 hours for CPE (cytopathic effect) under the white light microscope and expression of GFP under the fluorescent microscope. When all of the cells showed CPE, the 1° stock lysate was collected, and freeze/thaw cycles were performed as described above.

For secondary (2°) amplification, twenty 15-cm tissue culture dishes of 293A cells were prepared so that the cells were 80–90% confluent. All but 20 ml of 5% MEM media was removed, and each dish was inoculated with 300–500 ml 1° amplified rAdv lysate. After 48 hours the cells were lysed from virus production. The lysate was collected into 250-ml polypropylene centrifuge bottles.

To purify the rAdV, NP-40 detergent was added to a final concentration of 0.5% to the bottles of crude lysate to lyse all cells. Bottles were placed on a rotating platform for 10 minutes, agitating as fast as possible without the bottles falling over. The debris was pelleted by centrifugation at 20,000×G for 15 minutes. The supernatants were transferred to 250-ml polycarbonate centrifuge bottles, and 0.5 volume of 20% PEG-8000/2.5 M NaCl solution was added. The bottles were shaken overnight on ice. The bottles were centrifuged at 20,000×G for 15 minutes, and supernatants were discarded into a bleach solution. Using a sterile cell scraper, the precipitate from 2 bottles was resuspended in 2.5 ml PBS. The virus solution was placed in 2-ml microcentrifuge tubes and centrifuged at 14,000×G for 10 minutes to remove any additional cell debris. The supernatant from the 2-ml microcentrifuge tubes was transferred to a 15-ml polypropylene snapcap tube and adjusted to a density of 1.34 g/ml with CsCl. The volume of the virus solution was estimated, and 0.55 g/ml of CsCl was added. The CsCl was dissolved, and 1 ml of this solution weighed 1.34 g. The solution was transferred to polycarbonate thick-walled centrifuge tubes (3.2 ml) (Beckman #362305) and spun at 348,000×G for 34 hours at 25° C. in a Beckman Optima TLX microultracentrifuge with a TLA-100.4 rotor. The virus formed a white band. Using wide-bore pipette tips, the virus band was collected.

The virus preparation was desalted by gel filtration using commercially available columns and cross-liked dextran media (PD-10 column prepacked with Sephadex® G-25M; Pharmacia, Piscataway, N.J.). The column was equilibrated with 20 ml of PBS. The virus was loaded and allowed to run into the column. Five ml of PBS was added to the column, and fractions of 8–10 drops were collected. The optical densities of 1:50 dilutions of each fraction were determined at 260 nm on a spectrophotometer. A clear absorbance peak was present between fractions 7–12. These fractions were pooled, and the optical density (OD) of a 1:25 dilution was determined. Virus concentration was calculated by the formula: (OD at 260 nm)(25)(1.1×10$^{12}$)=virions/ml. The OD of a 1:25 dilution of the zalpha33 rAdV was 0.059, giving a virus concentration of 2.8×10$^{12}$ virions/ml.

To store the virus, glycerol was added to the purified virus to a final concentration of 15%, mixed gently but effectively, and stored in aliquots at -80° C.

A protocol developed by Quantum Biotechnologies, Inc. (Montreal, 3 5 Canada) was followed to measure recombinant virus infectivity. Briefly, two 96-well tissue culture plates were seeded with 1×10$^4$ 293A cells per well in MEM containing 2% fetal bovine serum for each recombinant virus to be assayed. After 24 hours, 10-fold dilutions of each virus from 1×10$^{-2}$ to 1×10$^{-14}$ were made in MEM containing 2% fetal bovine serum. 100 µl of each dilution was placed in each of 20 wells. After 5 days at 37° C., wells were read either positive or negative for CPE and a value for plaque forming units/ml (PFU) was calculated.

TCID$_{50}$ formulation used was as per Quantum Biotechnologies, Inc., above. The titer (T) was determined from a plate where virus used was diluted from 10$^{-2}$ to 10$^{-14}$, and read 5 days after the infection. At each dilution a ratio (R) of positive wells for CPE per the total number of wells was determined.

To calculate titer of the undiluted virus sample: the factor, "F"=1+d(S−0.5); where "S" is the sum of the ratios (R); and "d" is Log10 of the dilution series, for example, "d" is equal to 1 for a ten-fold dilution series. The titer of the undiluted sample is T=10$^{(1+F)}$=TCID$_{50}$/ml. To convert TCTD$_{50}$/ml to pfu/ml, 0.7 is subtracted from the exponent in the calculation for titer (T).

The zalpha33 adenovirus had a titer of 3.2×10$^{10}$ pfu/ml.

EXAMPLE 5

Approximately 10 µg pZytrack vector containing the sequence-confirmed mouse zalpha33 coding region was digested with FseI and AscI. The vector was then ethanol precipitated, and the pellet was resuspended in Tris-EDTA buffer. The released 537-bp zalpha33 fragment was isolated by running the digested vector on a 1.2% agarose gel (SeaPlaque™ GTG: FMC Corp., Rockland, Me.) and excising the fragment. DNA was purified using a commercially available kit (QiaQuick™ Gel Extraction Kit, Qiagen Inc.).

The mouse zalpha33 fragment was then ligated into the vector pTG12-8, which was previously digested with FseI and AscI. The pTG12-8 plasmid, designed for expression of a gene of interest in transgenic mice, contains an expression cassette flanked by 10 kb of MT-1 (mouse metallothionein gene) 5' DNA and 7 kb of MT-1 3' DNA. The expression cassette comprises the MT-1 promoter, the rat insulin II intron, a polylinker for the insertion of the desired clone, and the human growth hormone poly A sequence.

About one microliter of the ligation reaction mixture was electroporated into *E. coli* host cells (Electromax DH10B™ cells; Life Technologies) according to the supplier's directions, plated onto LB plates containing 100 µg/ml ampicillin, and incubated overnight at 37° C. Colonies were picked and grown in LB media containing 100 µg/ml ampicillin. Miniprep DNA was prepared from the picked clones and screened for the mouse zalpha33 insert by restriction digestion with EcoRI and agarose gel electrophoresis. Maxipreps of the correct pTG12-8 murine zalpha33 construct were performed.

A SalI fragment containing 5' and 3' flanking sequences, the MT promoter, the rat insulin II intron, murine zalpha33 cDNA and the human growth hormone poly A sequence was prepared and used for microinjection into fertilized mouse oocytes. Two transgenic mice with high zalpha33 expression levels had low white blood cell counts.

EXAMPLE 6

Four confluent T-162 flasks of HaCaT human keratinocyte cells (Boukamp et al., *J. Cell. Biol.* 106:761–771, 1988) were trypsinized. Each pellet was resuspended in 4 ml DMEM+5% FBS. The HaCat cells were transduced by adding purified mouse zalpha33 recombinant adenovirus (AdZy/zalpha33) or parental adenovirus at a MOI of 500 particles per cell and shaking slowly at 37° C. for 1 hour. The cells were then transfered to two T-162 flasks each containing 30 ml growth media and incubated 48 hours (until confluent). The cells were rinsed twice with 1×PBS and re-fed with 30 ml per flask serum-free/phenol-red-free DMEM containing L-glutamine, sodium pyruvate and HEPES buffer. The cells were incubated and harvested three times at 72-hour intervals. The collected conditioned media

EXAMPLE 7

Mouse zalpha33 was assayed in an aortic ring outgrowth assay (Nicosia and Ottinetti, *Laboratory Investigation* 63(1):115, 1990; Villaschi and Nicosia, *Am. J. Pathology* 143(1):181–190, 1993). Thoracic aortas were isolated from 1–2 month old SD female rats and transferred to petri dishes containing HANK's buffered salt solution. The aortas were flushed with additional HANK's buffered salt solution to remove blood, and adventitial tissue surrounding the aortas was carefully removed. Cleaned aortas were transferred to petri dishes containing serum-free basal medium (EBM; obtained from Clonetics, San Diego, Calif.). Aortic rings were obtained by slicing approximately 1-mm sections using a scalpel blade. The ends of the aortas used to hold the aorta in place were not used. The rings were rinsed in fresh EBM basal media and placed individually in wells of a 24-well plate coated with basement membrane matrix (Matrigel®; Becton Dickinson, Franklin Lakes, N.J.). The rings were overlayed with an additional 50 µl of Matrigel and placed at 37° C. for 30 minutes to allow the matrix to gel. Test samples were diluted in EBM basal serum-free media supplemented with 100 units/mil penicillin, 100 µg/ml streptomycin and HEPES buffer and added at 1 ml/well. Background control was EBM basal serum-free media alone. Basic FGF (R&D Systems, Minneapolis, Minn.) at 20 ng/ml was used as a positive control. AdZy/zalpha33 adenovirus was added to wells, assuming a cell count of 500,000 cells and a multiplicity of infection of 5000 particles/cell. A null pZyTrack adenovirus (zPar) was used as a control. 10× conditioned media generated in HaCat keratinocyte cells by a 4 day tranduction with the AdZy/zalpha33 at an MOI of 500 particles per cell was also used in this assay. A control conditioned media generated using the zPar rAdenovirus to transduce HaCat cells was used as the matching negative control. Samples were added in a minimum of quadruplets. Rings were incubated for 5–7 days at 37° C. and analyzed for growth. Aortic outgrowth was scored by multiple, blinded observers using 0 as no growth and 4 as maximum growth. Zalpha33/HaCat conditioned media generated by transduction with the AdZy/zalpha33 produced a significant increase in outgrowth as compared to controls, and was comparable to other potent growth factors (e.g., bFGF).

EXAMPLE 8

Various human tissues, including heart, pancreas, testis, liver, ovary and appendix, were isolated and screened for zalpha33 expression by in situ hybridization. 2 0 The tissues were fixed overnight in 10% neutral phosphate-buffered formalin (Surgipath, Richmond, Ill.), and embedded in paraffin (Oxford Scientific, St. Louis, Mo.) using standard techniques. Tissues were sectioned at 4 to 8 microns. Tissues were prepared using a standard protocol ("Development of non-isotopic in situ hybridization" at http://dir.niehs.nih.gov/dirlep/ish.html). Briefly, tissue sections were deparaffinized with a commercially available histological clearing agent HistoClear™; National Diagnostics, Atlanta, Ga.) and then dehydrated with ethanol. Next they were digested with 50 µg/ml Proteinase K (Boehringer Diagnostics, Indianapolis, Ind.) at 37° C. for 2 to 5 minutes. This step was followed by acetylation and re-hydration of the tissues.

An antisense probe was generated from the zalpha33 sequence using Sp6 RNA polymerase. The probe was labeled with digoxigenin (Boehringer) using a commercially available in vitro transcription system (Promega, Madison, Wis.) as directed by the manufacturer.

In situ hybridization was performed with the digoxigenin-labeled zalpha33 probe. The probe was added to the slides at a concentration of 1 to 5 pmol/ml for 12 to 16 hours at 57.5° C. Slides were subsequently washed in 2×SSC and 0.1×SSC at 55° C. The signals were amplified using a tyramide signal amplification kit (TSA™ Signal Amplification; NEN Life Science Products, Inc., Boston, Mass.) (see, U.S. Pat. Nos. 5,731,158; 5,583,001; and 5,196,306) and visualized with a commercially available substrate kit (Vector® Red; Vector Laboratories, Burlingame, Calif.) as directed by the manufacturer. The slides were then counterstained with hematoxylin (Vector Laboratories).

Signals were seen in the heart, pancreas, testis, liver, and appendix. The positive-staining cells appeared to be endothelial cells of vessels, immune cells, acinar cells of pancreas, and spermatocytes of testis.

From the foregoing, it will be appreciated that, although specific embodiments of the invention have been described herein for purposes of illustration, various modifications may be made without deviating from the spirit and scope of the invention. Accordingly, the invention is hot limited except as by the appended claims.

What is claimed is:

1. An expression vector comprising the following operably linked elements:
   a transcription promoter;
   a DNA segment encoding a polypeptide wherein the polypeptide comprises residues 18–178 of SEQ ID NO:2; and
   a transcription terminator.

2. The expression vector of claim 1 further comprising a secretory signal sequence operably linked to the DNA segment.

3. The expression vector of claim 2 wherein the secretory signal sequence encodes residues 1–17 of SEQ ID NO:2.

4. A cultured cell into which has been introduced the expression vector of claim 1, wherein said cell expresses said DNA segment.

5. The cell of claim 4 wherein the expression vector further comprises a secretory signal sequence operably linked to the DNA segment, and wherein the polypeptide is secreted by the cell.

6. The cell of claim 5 wherein the secretory signal sequence encodes residues 1–17 of SEQ ID NO:2.

7. A method of making a polypeptide comprising:
   culturing a cell into which has been introduced the expression vector of claim 1 under conditions whereby the DNA segment is expressed and the polypeptide is produced; and
   recovering the polypeptide.

8. The method of claim 7 wherein the expression vector further comprises a secretory signal sequence operably linked to the DNA segment, and wherein the polypeptide is secreted by the cell and recovered from a medium in which the cell is cultured.

9. The method of claim 8 wherein the secretory signal sequence encodes residues 1–17 of SEQ ID NO:2.

10. A polypeptide produced by the method of claim 7.

* * * * *